US005679364A

United States Patent [19]
Levy

[11] Patent Number: 5,679,364
[45] Date of Patent: Oct. 21, 1997

[54] COMPOSITIONS AND METHODS FOR REDUCING THE AMOUNT OF CONTAMINANTS IN AQUATIC AND TERRESTRIAL ENVIRONMENTS

[75] Inventor: Richard Levy, Fort Myers, Fla.

[73] Assignee: Lee County Mosquito Control District, Lehigh, Fla.

[21] Appl. No.: 479,119

[22] Filed: Jun. 7, 1995

[51] Int. Cl.$^6$ ................................... A01N 25/08
[52] U.S. Cl. .................. 424/405; 424/78.18; 424/406; 424/409; 424/417
[58] Field of Search ........................ 424/405, 406, 424/409, 417–419, 78.18; 435/262.5, 281, 821, 822

[56] References Cited

U.S. PATENT DOCUMENTS

| | | | |
|---|---|---|---|
| 3,676,357 | 7/1972 | Ciuti et al. | 252/259.5 |
| 4,076,663 | 2/1978 | Masuda et al. | 260/17.4 GC |
| 4,134,863 | 1/1979 | Fanta et al. | 260/17.4 GC |
| 4,230,801 | 10/1980 | Gutnick et al. | 435/101 |
| 4,276,094 | 6/1981 | Gutnick et al. | 134/10 |
| 4,389,513 | 6/1983 | Miyazaki | 525/186 |
| 4,525,527 | 6/1985 | Takeda et al. | 524/831 |
| 4,552,938 | 11/1985 | Mikita et al. | 526/240 |
| 4,612,250 | 9/1986 | Takeda et al. | 428/500 |
| 4,618,631 | 10/1986 | Takeda et al. | 521/109.1 |
| 4,654,393 | 3/1987 | Mikita et al. | 526/240 |
| 4,677,174 | 6/1987 | Alexander et al. | 526/240 |
| 4,703,067 | 10/1987 | Mikita et al. | 521/63 |
| 4,818,534 | 4/1989 | Levy | 424/404 |
| 4,983,389 | 1/1991 | Levy | 424/404 |
| 5,142,817 | 9/1992 | Rolf | 47/24 |
| 5,273,749 | 12/1993 | Bok et al. | 424/405 |
| 5,317,834 | 6/1994 | Anderson | 47/48.5 |

FOREIGN PATENT DOCUMENTS 8808821  11/1988  WIPO .

OTHER PUBLICATIONS

W.D. Garrett, "Confinement and Control of Oil Pollution on Water with Monomolecular Surface Films", *Proceedings from Joint Conference on Prevention and Control of Oil Spills*, 257–261 (Dec. 15–17, 1969).
W.D. Garrett et al., "Control and Confinement of Oil Pollution on Water with Monomolecular Surface Films", *NRL Memorandum Report 2451*, (Jun. 1972).
The Role of Chemical Dispersants in Oil Spill Control, *American Petroleum Institute Spills Technology Issue Group* (Jan., 1986).
Alcosorb AB3—Water–Retention Aid for Soil and Growing Media, *Allied Colloids*.
Hoechst Celanese—Superabsorbent Materials, *Sanwet Superabsorbent Products* (Aug., 1987).
IM–3500 Toxicity Testing Summary (Nov. 7, 1988).
Alcosorb—Water–Retention Aid for Soil and Growing Media, *Allied Colloids*.
Studies in Polymer Science 8; *Absorbent Polymer Technology*; Lisa Brannon–Peppas, editor; Elsevier Science Publishing Company Inc. (1990).
Characteristics of Competitive Agricultural Superabsorbents, *Allied Colloids*.
Acute Biomonitoring Results for Sea Sweep Inc.'s Oil Spill Absorbent Product, *T.H.E. Laboratories, Inc.* (Aug. 14, 1991).
Stockosorb—Absorbent Polymers (1992 Stockhausen).
The Absorber—News about Absorbent Polymers; *Information from Stockhausen* (Jan. 1992.).
The Absorber—News about Absorbent Polymers; *Information from Stockhausen* (Feb. 1993.).
Sea Sweep brochure, *Sea Sweep Inc.*, (1993).
Sea Sweep—Solutions for oil and chemical spill cleanup on land and water, (Sep. 7, 1993).
Sea Sweep (Nov. 11, 1993).
Culigel, Stockhausen, Inc. (1994).
Superabsorbent Polymers—Science and Technology; *ACS Symposium Series 573;* Fredric L. Buchholz et al., editor (1994).
Handbook of Bioremediation; John E. Matthews, project officer; Lewis Publishers (1994).
Hydrocarbon Bioremediation; Robert E. Hinchee et al., editors; Lewis Publishers (1994).
1994 Annual book of ASTM Standards; Section 11—Water and Environmental Technology, 1544–.
Groundwater Technology, Inc. Bioremediation Services (Feb. 1994).
"Guidelines for Assessment and Remediation of Petroleum Contaminated Soil," Prepared by Florida Department of Environmental Protection, Division of Waste Management (May 1994).
"Health and Environmental Research Publications," American Petroleum Institute (Sep. 1994).
Bio–Systems Corporation (Fall 1994).
"MonoSolutions," *MonoSol Water Soluble Packaging Films,* IV (Oct., 1994).
"Bioremediation Statement of Qualifications," Sybron Chemicals, Inc. (Jan. 1995).

(List continued on next page.)

*Primary Examiner*—Neil S. Levy
*Attorney, Agent, or Firm*—Schwegman, Lundberg, Woessner & Kluth, P.A.

[57] ABSTRACT

The invention provides contaminant-reducing agent delivery compositions that are useful for the control of organic or inorganic contaminants in aquatic or terrestrial environments. The compositions comprise one or more superabsorbent solid organic polymers and at least one contaminant-reducing agent. These superabsorbent polymers act as the primary carriers of one or more contaminant-reducing agents effective for the control of organic or inorganic contaminants in aquatic or terrestrial environments. Contaminant-reducing agents include film-forming agents, microbial agents, nutrient agents, and mixtures thereof. The invention also provides a method to entrap and accumulate organic and inorganic contaminants in one or more superabsorbent polymer compositions containing no contaminant-reducing agent. The invention also provides a method to entrap water in superabsorbent polymers to activate natural and applied microbial and nutrient contaminant-reducing agents in terrestrial environments.

18 Claims, No Drawings

OTHER PUBLICATIONS

"Lab developing suicidal waste–eating microbes," *News Press* (Jan. 8, 1995).

John K. Borchardt, "Dealing with Soil Contaminants," *Today's Chemist at Work*, 4 47, 49, 51–52 (Mar. 1995).

Ronald M. Atlas, "Bioremediation," *Chemical and Engineering News*, 32–42 (Apr. 3, 1995).

Thomas B. Reed et al., "A Hydrophobic Oleophilic Form of Biomass for Oil and Chemical Absorption," *Presented at Advances in Thermochemical Biomass Conversion Conference*, Interlaken, Switzerland (May 11–15).

Franz K. Hiebert, "Bacterial Degradation of Petroleum," *Alpha Environmental, Inc.*

Robert E. Miller of Grain Processing Corporation to Dr. Richard Levy, Subject: WATER LOCK® G series toxicologic testing.

"Polymer," SNF Floerger.

"Our Reputation for Quality is Recognized Around the World," Sybron Chemicals, Inc.

"Bioremediation Techniques," Sybron Chemicals Inc.—Biochemical Division.

"A Commitment to Manufacturing Excellence and Quality," *Specialty Products*.

"AquaStore—Absorbant Polymer," *Cyanamid*.

"Superabsorbent Polymer—Aqua Keep®" *Seitetsu Kagaku Co., Ltd.*

"AquaStore Soil Additive," *Cyanamid*.

"Terra–Sorb," *Industrial Services International, Inc.*

"Favor Absorbent Polymers," *Stockhausen*.

"When Oil Spills, Most People Lower the Boom . . . ," *Sea Sweep*.

"Superabsorbent Polymers—a contribution to modern industries and emerging technologies," *Stockhausen*.

"Favor Absorbent Polymers—Favor SAB 900," *Stockhausen*.

"StockoSorb—Superabsorbent Polymers for Agricultural Applications," *Stockhausen*.

"Favor C—Superabsorbent Polymers for Power & Communications Cable Applications," *Stockhausen*.

"SGP Absorbent Polymer," *General Mills Chemicals Inc.*

"Dissolvo–Pouch 45," *Gilbreth International Corporation*.

"Water Lock® G–404 Superabsorbent Polymer," *Grain Processing Corporation*.

"Product Data: ABR Diesel Blend," *Sybron Biochemical*.

"Product Data: ABR Gasoline Blend," *Sybron Biochemical*.

"Product Data: Bi–Chem Accelerators," *Sybron Biochemical*.

"Product Data: Sybron ABR Activator III," *Sybron Biochemical*.

"Product Data: Sybron ABR Bio–Track Dol.," *Sybron Biochemical*.

"Product Data: ABR Hydrocarbon Blend," *Sybron Biochemical*.

"MonoSol," *Chris Craft Industrial Products, Inc.*

"Product Data Sheets" for *Polymer Films Inc.*

"StockoSorb—400 Series Superabsorbent Polymers Agricultural & Horticultural Applications," *Stockhausen*.

"Product Data Sheet—Water Lock L–Series," *Grain Processing Corporation*.

"Product Data Sheet—Water Lock A–100 Series—Superabsorbent Polymers".

"Product Data Sheets," *Grain Processing Corporation*.

"Product Data Sheet—Aqua Keep J–400," *Seitetsu Kagaku Co., Ltd.*

"Dow XU 43408.00 Superabsorbent Polymer".

COMPOSITIONS AND METHODS FOR REDUCING THE AMOUNT OF CONTAMINANTS IN AQUATIC AND TERRESTRIAL ENVIRONMENTS

BACKGROUND OF THE INVENTION

During this century, the demand for petroleum as a source of energy and as a primary raw material for the petrochemical industry has resulted in an increase in world production from 29 to over 2,400 million metric tons per year. This dramatic increase in the production, refining and distribution of crude oil has also brought with it an ever-increasing problem of environmental pollution. In part, this has been a consequence of the massive movements of petroleum by oil tankers from the areas of high production to those of high consumption. It has been estimated that 0.5% (12 million metric tons per year) of transported crude oil finds its way into sea water, largely through accidental spills and deliberate discharge of ballast and wash waters from oil tankers.

The toxicity of crude and refined oil to the environment and, even more directly, to man is well documented (D. F. Boefsch et al., "Oil Spills and the Marine Environment", Ballinger Publ., Cambridge, 1974 114 pp.; A. Nelson-Smith in the collected papers edited by P. Hepple, "Water Pollution by Oil", Elsevier, N.Y., 1971, pp 273–80) and need not be discussed in detail. It is sufficient to state that crude oil contains mutagenic, carcinogenic and growth inhibiting chemicals and that even small quantities (5–100 mg per liter) of certain petroleum fractions destroy microalgae and juvenile forms of microorganisms. Furthermore, it has been reported (I. Chett et al., Nature, 261, 308–9 (1976)) that petroleum inhibits microbial decomposition of organic matter in sea water by interfering with the ability of the microorganisms involved to move or orient themselves. Put simply, oil pollution in the ocean in general and in the coastal waters in particular presents a serious problem to commercial fisheries, recreational resources and public health.

Oil pollution is only one source among many which contaminate the environment. Environmental pollutants also include non-petroleum organic contaminants, which can be generated from various sources. Such organic and inorganic contaminants can be found in industrial waste produced by carpet and textile mills, pulp and paper mills, citrus processing plants, commercial kitchens, fast food restaurants, and food processing plants, for example. Such organic contaminants include pesticides, such as herbicides, growth inhibitors, growth regulators, sterilants, and the like.

Different approaches to reducing the concentration of environmental contaminants have been explored. One such approach is bioremediation, which is the use of living organisms to break down organic and inorganic contaminants into more basic components, remove environmental pollutants, restore contaminated sites, and prevent the accumulation of further pollutants. Generally, bioremediation is accomplished using bacteria, although other microorganisms, namely fungi and algae, have been used. See, for example, Ronald M. Atlas, Chemical & Engineering News, Apr. 3, 1995, pp. 32–42. There still exists a need, however, to reduce the amount of organic and inorganic contaminants in aquatic and terrestrial environments.

SUMMARY OF THE INVENTION

The present invention provides a contaminant-reducing composition comprising a contaminant-reducing agent and a superabsorbent solid organic polymer for delivery of the contaminant-reducing agent, wherein said composition is capable of reducing the amount of an organic or inorganic contaminant in an aquatic or terrestrial environment. The composition may be solid or liquid. If liquid, the composition is preferably capable of being sprayed, pumped, or injected. The composition may also be a controlled-release composition.

Preferably, the superabsorbent polymers are hydrophilic acrylamide and acrylate polymers which then act as matrices for the controlled release (e.g., fast, slow, pulsed, delayed) of the contaminant-reducing agent employed, according to zero-order, first-order, or square-root-of-time kinetics. More preferably, the superabsorbent polymer of the present invention is a combination of a polysaccharide and an organic monomer, oligomer, polymer, copolymer, terpolymer or tetrapolymer. Most preferably, the superabsorbent polymer of the present invention is the product of grafting amylopectin with acrylonitrile. Such superabsorbent polymers can also used by themselves (i.e., without the contaminant-reducing agent) to entrap and accumulate organic and inorganic contaminants, thereby preventing leaching or movement and further damage to areas of the environment that are far removed from the initial point(s) of contamination. The compositions may further include one or more non-toxic adjuvants or diluents.

In one embodiment of the invention, the contaminant-reducing agent comprises a film-forming agent. In another embodiment of the invention, the contaminant-reducing agent includes a microbial agent, such as bacteria, algae, and fungi, or combinations thereof, which are known to have bioremedial utilities against organic and inorganic contaminants. In yet another embodiment of the invention, the contaminant-reducing agent can also include a nutrient agent or complex to enhance the activity of the microbial agent(s). Alternatively, the nutrient agent or complex can be used alone with the superabsorbent polymer and applied to the environment to enhance the activity of microbial agents in the environment. The contaminant-reducing compositions can also include non-toxic adjuvants or diluents. Various combinations of the above-listed contaminant-reducing agents can be used.

The present invention also provides a method of reducing the amount of organic or inorganic contaminants in an aquatic or terrestrial environment. The method involves applying the contaminant-reducing composition described above to the contaminated site. Upon application, the contaminant-reducing agent impregnated in the superabsorbent polymer is released into the environment. Preferably, this release occurs in a controlled manner. Release of the contaminant-reducing agent can occur, for example, via a water-activated swelling-controlled diffusion process, and/or the biodegradation (i.e., microbial) or degradation (e.g., decomposition via ultraviolet light) of the polymer.

In addition, the present invention provides a method of entrapping and accumulating organic or inorganic contaminants in an aquatic or terrestrial environment. The method involves contacting a superabsorbent solid organic polymer, a superabsorbent polymer laminate, a superabsorbent polymer composite, a superabsorbent polymer foam, or a superabsorbent polymer-loaded device with the contaminants in an amount effective to entrap and concentrate the contaminants to facilitate their removal.

Finally, the present invention provides a method for entrapping water in surface or subsurface areas of a terrestrial environment by adding a superabsorbent solid organic polymer in proximity to natural or applied microbial or nutrient contaminant-reducing agents, thereby improving the bioremediation of contaminants by providing the moisture necessary for enhanced microbial growth and nutrient activation.

DETAILED DESCRIPTION OF THE INVENTION

Surprisingly, it has been found that certain superabsorbent polymers are useful as matrices for contaminant-reducing agents effective for reducing the concentration of organic and inorganic contaminants, in aquatic or terrestrial environments, with a single application or multiple applications of a solid or liquid formulation. These compositions may be in controlled-release form.

Superabsorbent polymers, including starch graft copolymers, are well known in the art. See, for example, those described in U.S. Pat. No. 4,375,535 (Kightlinger et al.), and U.S. Pat. No. 4,497,930 (Yamasaki et al.). These polymers have been used as adhesives, flocculents, and as water-retaining materials for agricultural or sanitation uses. Superabsorbent polymers have also been used alone in pest management applications or in combination with pesticides or insecticides as matrices for their release in aquatic or terrestrial environments. However, the advantages of using this class of polymers as contaminant-entrapment matrices, as matrices for water-activation of contaminant-reducing agents, and as matrices for the controlled release of active agents in aquatic or terrestrial environments to control organic or inorganic contaminants have gone unrecognized until the present invention.

A. Superabsorbent Polymers

It has been observed that certain superabsorbent polymers that are impregnated with one or more contaminant-reducing agents have the ability to swell in water and/or biodegrade/degrade, and thereby release the substance(s) contained therein. Furthermore, it has been observed that the superabsorbent polymers that swell when exposed to water also have the ability to reform or contract to a consistency similar to their original form when evaporation has caused the water to be removed from the polymer matrix, and then reswell with additional exposure to water. This ability to be functional after repetitive periods of exposure to water is advantageous for pretreatment and/or prolonged controlled release applications. Certain superabsorbent polymers also have the ability to entrap and accumulate, i.e., concentrate, contaminants to facilitate their removal. Also, certain superabsorbent polymers (e.g. starch-graft) applied to terrestrial habitats can promote the degradation of contaminants by natural or applied microorganisms by entrapping water in surface or subsurface areas, and thereby provide higher and prolonged moisture levels and added nutrients (i.e., starch) for enhanced microbial growth and development. Similarly, the water entrapped within superabsorbent polymers can also activate and prolong the activity of natural or applied nutrient contaminant-reducing agents.

The superabsorbent polymers useful in the compositions and methods of the present invention are synthetic organic polymers that are solid and hydrophilic. They are capable of absorbing over 100 times their weight in water. Generally, these superabsorbent polymers are chosen from acrylamide and acrylate polymers, including copolymers, terpolymers, tetrapolymers, etc. These superabsorbent polymers are typically in a powder or flake form, adapted to be blended and/or agglomerated. Superabsorbent polymers are generally nontoxic, biodegradable, UV degradable, or erodible, and relatively inexpensive to buy or produce.

The acrylamide and acrylate superabsorbent polymers may be, for example, acrylamide alkali metal or alkali metal/aluminum acrylate copolymers; propenenitrile homopolymers, hydrolyzed, alkali metal or alkali metal/aluminum salts; polymers of propenamide and propanoic acid, alkali metal salts; hydrolyzed acrylonitrile copolymers, and starch graft copolymers and terpolymers thereof. All of these are designed to be hydrophilic.

The hydrophilic superabsorbent polymers of the present invention can absorb over one hundred, more typically over 500, times their own weight in water (measured using distilled water, pH 7.5, 25° C., 760 mm Hg, absorption within 30 seconds). Certain of these polymers can absorb over 1,000, and even over 5,000, times their weight in water. However, the absorption or swelling capacity and absorption or swelling time typically varies with each specific superabsorbent polymer. Additionally, both swelling and shrinkage occurs in a terrestrial environment. Water and soil quality (e.g., pH, salinity) will effect the degree of swelling of the superabsorbent polymer(s) in aquatic and terrestrial environments.

One exemplary class of superabsorbent polymers suitable for use in the present invention includes a combination of polysaccharide and organic monomers, oligomers, polymers, copolymers, terpolymers, or tetrapolymers, etc. The two components may be combined, for example, by the methods described in U.S. Pat. No. 4,375,535 (Kightlinger et al.), and U.S. Pat. No. 4,497,930 (Yamasaki et al.). For example, a suitable superabsorbent polymer for use in the present invention would be the product of grafting corn starch (amylopectin) with acrylonitrile (an acrylic monomer or oligomer). Another exemplary class of superabsorbent polymers includes propanoic or acrylonitrile/acrylamide-base, oligomers, polymers, copolymers, terpolymers or tetrapolymers, etc., that also show superabsorbency properties.

Non-limiting specific examples of superabsorbent polymers with differential swelling properties that are particularly useful in the method of the present invention include: a copolymer of acrylamide and sodium acrylate (TERRA-SORB GB, available from Industrial Services International, Inc., Bradenton, Fla.); hydrolyzed starch-polyacrylonitrile (TERRA-SORB available from Industrial Services International, Inc., Bradenton, Fla.); 2-propenenitrile homopolymer, hydrolyzed, sodium salt or poly(acrylamide-co-sodium acrylate) or poly(2-propenamide-co-2-propanoic acid, sodium salt) (WATER LOCK Superabsorbent Polymer G-100 available from Grain Processing Corp., Muscatine, Iowa); starch-g-poly(2-propenamide-co-2-propanoic acid, sodium salt) (WATER LOCK Superabsorbent Polymer A-100, A-120, A-140, A-180 series, A-200, available from Grain Processing Corp., Muscatine, Iowa); starch-g-poly(2-propenamide-co-2-propanoic acid, mixed sodium and aluminum salts) (WATER LOCK Superabsorbent Polymer A-222 available from Grain Processing Corp., Muscatine, Iowa); starch-g-poly(2-propenamide-co-2-propanoic acid, potassium salt) (WATER LOCK Superabsorbent Polymer B-204, available from Grain Processing Corp., Muscatine, Iowa); poly(2-propenamide-co-2-propanoic acid, sodium salt) (WATER LOCK Superabsorbent Polymer G-400 available from Grain Processing Corp., Muscatine, Iowa); WATER LOCK L-Series Superabsorbent Laminates (L-413, L-415, L-435, L-513), available from Grain Processing Corp., Muscatine, Iowa; poly-2-propanoic acid, sodium salt (WATER LOCK Superabsorbent Polymer J-500 available from Grain Processing Corp., Muscatine, Iowa); starch-g-poly(acrylonitrile) or poly(2-propenamide-co-sodium acrylate) (SGP 502S, available from General Mills Chemicals Inc., Minneapolis, Minn.); starch/acrylonitrite copolymer (SUPER SORB, AGRIGEL, available from Super Absorbent Co., Lumberton, N.C.); crosslinked copolymers of acrylamide and sodium acrylate (AQUASORB PR-3005, (A, B, C, K), 005, available from SNF Floerger, France); acrylamide/sodium polyacrylate crosslinked polymers (ALCOSORB AB3C, AB3S, RD, available from Allied Colloids, Inc., Suffolk, Va.); anionic polyacrylamide (AQUASTORE Absorbent Polymer, available from American Cyanamid Co., Wayne, N.J.); starch grafted sodium polyacrylates (SANWET IM-1000, IM-1500, IM-3500, IM-3900, IM-5600 Superabsorbent Polymer Series, SANWET IM-1000, and IM-1500 Laminates and SAMFOAM superabsorbent foams, available from Hoechst Celanese, Portsmouth, Va.); acrylic acid polymers, sodium salt (AQUA KEEP J-400, J-500, J-550 Superabsorbent Polymer Series, available from Sumitomo Seika Chemicals Co., Ltd., Osaka, Japan); crosslinked potassium polyacrylate/polyacrylamide copolymers (STOCKOSORB 300K and 400K Series, available from Stockhausen, Inc., Greensboro, N.C.); sodium polyacrylate (FAVOR SAB 100, SAB 800, SAB 900, SAB 954 Series, available from Stockhausen, Inc., Greensboro, N.C.); FAVOR/STOCKOSORB nonwoven, film, or fiber superabsorbent polymer laminates and composites, available from Stockhausen, Inc., Greensboro, N.C.; partial sodium salt of crosslinked polypropenoic acid (XU 40346.00 Superabsorbent Polymer, available from Dow Chemical Co., Midland; Mich.); potassium polyacrylate, lightly crosslinked (ARIDALL 1125, 1125 0, 1125 J, 1125 S, 1125 C, 1460 Superabsorbent Polymer Series, available from Chemdal Corporation, Arlington Heights, Ill.); sodium polyacrylate, lightly crosslinked (ASAP 1000, ASAP 1100, 1430, available from Chemdal Corporation, Arlington Heights, Ill.); sodium polyacrylates (NORSOCRYL B 50, B 65, S 35, S 45, D 50, D 60, D 65 Series, available from Elf Atochem, France); poly(sodium acrylate) homopolymer (SS Superabsorbent Polymer, available from Absorbent Technologies, Inc., Muscatine, Iowa).

B. Contaminant-Reducing Agents

As used herein, the term "contaminant-reducing agent" means a compound or substance that is capable of controlling or reducing the amount of organic or inorganic contaminants in an aquatic or terrestrial environment needing such treatment, either directly or indirectly.

Organic and inorganic contaminants, as well as nonpetroleum organic contaminants, include those found in industrial waste, such as those from textile and paper mills, citrus processors, chemical manufacturers, and transportation facilities, as well as restaurants and institutions, such as commercial kitchens, food processing plants, and the like. Other sources of contaminant production include crude oil spills, chemical and solvent leaks, fuel oil leaks, and creosote contamination. Inorganic contaminants include, for example, inorganic sulfur and ferrous compounds, metallic elements, as well as heavy metals, such as mercury, and certain other copper compounds used as herbicides and algicides.

Organic contaminants include various pesticides, such as insecticides, growth regulators, growth inhibitors, toxicants, bactericides, attractants, repellants, hormones, molluscicides, defoliants, chemosterilants, fumigants, systemics, rodenticides, avicides, detergents, surfactants, nematicides, acaricides, miticides, predicides, herbicides, agricultural chemicals, algicides, fungicides, sterilants; polycyclic aromatic hydrocarbons (PAH's), polychlorinated biphenyls (PCB's), greasy wastes, solvents, crude oil, diesel fuel, waste oil, Bunker "C" oil, phenolics, halogenated hydrocarbons, citrus juice processing wastes, terpene alcohols, starchy carbohydrates, and the like. Examples of specific organic contaminants include anthracene, chlorotoluenes, chrysene, cresols, di-N-octylphthalate, dichlorobenzene, dichlorethanes, dichloropropanes, dichlorotoluene, 2-ethoxyethanol, ethylene glycol, ethylene glycol monoethyl ether acetate, ethylbenzene, fluorene, isoprenoids, methyl ethyl ketone, methylene chloride, naphthalene, pentachlorophenol, phenanthrene, 1,1,2,2-tetrachloroethane, toluene, 1,1,2-trichloroethane, trichloroethylene, benzoate, chlorobenzoates, methanol, ethyl acetate, cyclohexanone, ethylbenzene, 2,4-dichlorophenoxyacetic acid, 2,4,5-trichlorophenoxyacetic acid, m,o,p-xylene, butyl acetate, camphor, hexane, heptane, octane, nonane, d-limonene, linalool, geraniol, citronellol.

Contaminant-reducing agents for use in the superabsorbent polymer-based compositions include film-forming agents, aerobic or anaerobic microbial agents, and nutrient agents. These can be used singly or in various combinations. In a preferred embodiment, the contaminant-reducing agent comprises at least one film-forming agent. The use of a film-forming agent in combination with another contaminant-reducing agent generally acts to enhance the activity of the second agent. For example, when used in combination with a microbial agent, because microbial agents of the present invention are generally aerobic and must operate at the oil/water interface to control floating oil, film-forming agents can be used to increase the surface area of the oil spill while uniformly spreading the microbial agent throughout a thin layer of dispersed oil, thereby accelerating the biodegradation process. Not only is the oil made more readily available to the microbial agent, but mixing and dilution of emulsion droplets in a greater volume of water assures a more adequate supply of nutrients for the microbial agent utilized. In another bioremediation approach for this type of dual action treatment, the composition containing a film-forming agent can be applied around the perimeter of an aquatic oil spill to help concentrate the dispersed oil at the surface of the water, with for example, booms, to compact and decrease the surface area of the oil spill, while simultaneously releasing and spreading the microbial agent to contact the perimeter of the compacted oil for prolonged periods. A single microbial agent composition could then be dispersed uniformly over the confined oil spill to assure optimal and prolonged bioremediation throughout the oil spill as well as around the oil spill perimeter.

1. Film-Forming Agents

As used herein, the term "film-forming agent" is meant to include dispersants, surface-active agents, surfactants, detergents, and the like. Typically, this class of chemicals have an oil-soluble end (i.e., a hydrocarbon chain) and a water soluble end (i.e., polar groups, such as carboxylate, sulfonate, ether, alcohol, or polyethylene oxide). Because of this dual nature, film-forming agents orient at the surface contaminant/water interface. Surface contaminants refer to contaminants which have a tendency to float on the surface of water. Specific examples of surface contaminants include oil or petroleum. When applied around the perimeter of an oil spill, for example, a film-forming agent will reduce the surface tension of the water while spontaneously and rapidly spreading over the surface of the water to form a near monomolecular or duplex film that can push or concentrate oil or other surface contaminants into a confined area for clean-up via conventional mechanical sponging, suction, or removal equipment. Alternatively, when applied to oil, the oriented film-forming molecules can also reduce the interfacial tension between the oil and water thereby "weakening" and reducing the cohesiveness of the oil slick.

Additionally, the hydrophilic groups of the film-forming molecules on the surface of the oil droplets repel other droplets and prevent coalescence. The hydrophilic surface also reduces the tendency of the droplets to stick to solid surfaces such as marine sediments, shorelines, and plants. By preventing oil from sticking to marine sediments, film-forming agents thus prevent oil from sinking.

Film-forming agents that are suitable for use in the present invention are generally more oil soluble than water soluble and preferably are only minimally water soluble. Furthermore, film-forming agents suitable for use in the present invention are organic materials which spread rapidly and spontaneously into extremely thin films approaching monomolecular dimensions. Consequently, small quantities of film-forming agents will affect large areas of a water surface. These film-forming agents are generally autophobic, nonionic, nonvolatile organic liquids with a density less than water. Typically, they have a low freezing point and a boiling point above the maximum air temperature of the environment into which they are placed. The freezing point can be below about 5° C. The boiling point can be about 170° C. or higher, preferably it is at least about 200° C. These film-forming agents have an HLB (Hydrophile Lipophile Balance) number of 10 or less, a bulk viscosity of less than 1000 centistokes at the temperature of use, a surface tension effectiveness which lowers the surface tension to approximately 35 dynes/cm or less, and are generally capable of rapidly and spontaneously spreading with high spreading potentials.

Suitable film-forming agents include, but are not limited to, POE-2-isostearyl alcohol, sorbitan monooleate, sorbitan trioleate, sorbitan monolaurate, oxyethylated oleyl alcohol having two oxyethylene groups, diethylene glycol monolaurate, oxyethylated lauryl alcohol having four oxyethylene groups, an oxyethylated branched alkanol of 15–19 carbon atoms, unsaturated cis-alkanol of 12–18 carbon atoms and up to five oxyethylene groups, and an unsaturated cis-alkanol of 15–19 carbon atoms. These film-forming agents can be used in combination with an alcohol such as 2-ethyl butanol, for example. Most preferably, the film-forming agent is selected from the group consisting of POE-2-isostearyl alcohol, 65% sorbitan monolaurate and 35% 2-ethyl butanol, and 75% sorbitan monooleate and 25% 2-ethyl butanol.

2. Microbial agents

As used herein, the term "microbial agents" is meant to include microorganisms that enhance biodegradation processes. These microorganisms include bacteria, fungi, and algae, or combinations of these microorganisms, for example. Furthermore, as used herein, "biodegradation" means the chemical alteration and breakdown of a substance to usually smaller products caused by microorganisms and their enzymes. Contaminants that are biodegradable include any compound that can be microbially mineralized into carbon dioxide, water, ammonia and/or chloride, or that can be transformed into a non-hazardous intermediate. "Bioremediation" refers to the use of living organisms, primarily microorganisms, to convert harmful organic or inorganic contaminants into carbon dioxide, water, cell tissue, and energy, to remove pollutants from the environment, to restore contaminated sites, and to prevent further pollution from accumulating. Generally, contaminants amenable to bioremediation include: petroleum hydrocarbons, such as gasoline, diesel, fuel oil, crude oil, refinery sludges; aromatics, such as benzene, toluene, xylene, ethylbenzene, styrene; polynuclear aromatic hydrocarbons, such as naphthalene, phenanthrene, pyrene, benzo[a]pyrene; alcohols, such as isopropanol, ethanol, ethylene glycol, t-butanol; carbohydrates, animal fats and greases; detergents; ketones, such as acetone, methyl ethyl ketone; phenols, such as chlorophenol, pentachlorophenol; polychlorobiphenyls; phthalates; chlorinated solvents, such as methylene chloride, ethylene dichloride.

A wide variety of petroleum degrading microorganisms have been found to bioemulsify hydrocarbons and are thus suitable for use in the present invention. These emulsions are microbiological in origin, and appear to be mediated either by the cells themselves of by the production of extracellular emulsifying agents. For example, the growth of *Mycobacterium rhodochrous* NCIB 9905 on n-decane yields an emulsifying factor which was reported by R. S. Holden et al. (*J. Appl Bacteriol.*, 32, 448 (1969)) to be a nonionic detergent. J. Tguchi et al. (*Agric. Biol. Chem.*, 33, 1657 (1969)) found that *Candida petrophilium* produced an emulsifying agent composed of peptides and fatty acid moieties, while T. Suzuki et al. (*Agric. Biol. Chem.*, 33, 1619 (1969)) found trehalose lipid in the oil phase of culture broths of various strains of Arthrobacter, Brevibacterium, Corynebacterium and Norcardia.

*Torulopsis gropengiesseri* was found to produce a sophorose lipid, while rhamnolipids are reported by K. Hisatsuka et al. (*Agric. Biol Chem.*, 36, 2233 (1971)) to have been produced by *Pseudomonas aeruginose* strain S7B1 and by S. Itoh et al. (*Agric Biol. Chem.*, 36, 2233 (1971)) to have been produced by another *P. aeruginose* strain, KY4025. The growth of *Corynebacterium hydrocarbolastus* on kerosene was reported by J. E. Zajic and his associates (*Dev. Ind. Microbiol.*, 12, 87 (1971); *Biotechnol. Bioeng.*, 14, 331 (1972); *Chemosphere*, 1, 51 (1972); *Crit. Rev. Microbiol.*, 5, 39 (1976) U.S. Pat. No. 3, 997,398) to produce an extracellular heteropolysaccharide which, among other properties, emulsified kerosene, Bunker C fuel and other fuel oils. U.S. Pat. No. 3,941,692 describes the use of an Arthrebacter species RAG-1 to clean oil-contaminated tank compartments by allowing the organism to aerobically grow on the oily wastes in such tanks using sea water containing added nutrients.

Several other microbial organisms have been known to have a variety of bioremedial applications as well. A toluene-resistant strain of Pseudomonas bacteria is being researched for bioconversions into nonaqueous solvents. *Pseudomonas fluorescens* strain HK44 was engineered to catabolize naphthalene and will be used to treat naphthalene-contaminated soil. *Acetobacter liquefaciens* S-1 bacteria are known to consume azo dyes. Iron- and sulfur-oxidizing bacterium, Thiobacillus ferrooxidans has been used to consume inorganic sulfur from industrial air emissions. Removal of organic sulfur-containing compounds from fossil fuels has been accomplished using Rhodococcus bacteria, which biodegrade dibenzothiophenes and other organosulfur compounds. Algae have also had several bioremedial applications as well. *Cholorococcum littorale* can tolerate high levels of carbon dioxide, which the algae converts into polysaccharides. *Prasinococcus capusulatus* is being studied for its ability to remove carbon dioxide from the atmosphere. Marine organisms such as foraminifera have demonstrated abilities to convert carbon from carbon dioxide into calcium carbonate. All of these microorganisms are discussed in Ronald M. Atlas, *Chemical & Engineering News*, Apr. 3, 1995, pp. 32–42.

Certain fungi have also been known to degrade straight and branched alkanes. Examples of such fungi include *Candida lipolytica* and *Aspergillus versicolor*.

Other microbial agents, particularly bacteria, that are suitable for use in the present invention can be broken into three broad categories: those that are capable of utilizing straight chain alkanes as a food source; those that metabolize cyclic alkanes; and those that are capable of metabolizing aromatics.

Many types of bacteria have evolved that can utilize straight and branched alkanes as a sole carbon and energy source. Fuhs, *Der mikrobiella Abban von Kohlenwasserstoffen. Arch Microbiol.*, 39, 374 (1961). There are fewer known species that degrade branched chain compounds than degrade straight chain alkanes. Furthermore, two-branched alkanes are easily degraded but three-branched alkanes are significantly more recalcitrant to metabolism. Examples of this type of bacteria that are suitable for use in the present invention include, but are not limited to, *Pseudomonas propanica, P. aeruginosa, Achromobacter sp., Flavobacterium sp., Micrococcus paraffinae, Corynebacterium flavum, Mycobacterium flavum, M. methanicum, M. perrugosum, M. rubrum, M. paraffinicum, M. sp., Nocardia sp.*, Cyclic alkanes are abundantly produced in nature by plants and microorganisms and are preserved in crude oil and other geologically stored hydrocarbons. Cyclic alkanes form a part of carotenoids as well as plant terpenoids, and are incorporated into the lipids of many bacteria. Cyclic alkanes are the most recalcitrant fraction of petroleum of bacterial degradation, yet microbes are known that utilize these compounds. Examples of this type of bacteria that are suitable for use in the present invention include, but are not limited to *Acetobacter suboxydans, Achromabacter sp., Acinebacter anitratum,* A. NCIB 9871, *Alcaligenes faecalis S6B1, Arthrobacter sp., Bacterium aliphaticum, Corynebacterium cyclohaxicum, Flavobacterium sp., Methylococcus capsulatus, Mycobacterium convolutum* strain R-22, *M. rhodochrous, M. vaccae* strain JOB-5, *Nocardia globulera* CL-1, *N. petroleophila* NCIB 9438, *N. sp., Pseudomonas aeruginosa* strain 473, P. C4, *P. fluorescens, P. methanica, P. mendocina, P. olevorans,* P. NCIB 9872, and *P. sp.*

The bacterial degradation of the aromatic fraction of petroleum has been studied in great detail. Gibson, "Biodegradation of Aromatic Petroleum Hydrocarbons", in *Fate and Effect of Petroleum Hydrocarbons in Marine Ecosystems and Organisms,* D.A. Wolfe ed., New York, Pergamon Press, p.36–46 (1977). Many types of bacteria have been identified as capable of utilizing aromatic hydrocarbons as a carbon and energy source, but Pseudomonas is the most prevalent and best studied genus. Examples of this type of bacteria that are suitable for use in the present invention include, but are not limited to, *Pseudomonas putida, P. putida* (39/D), *P. putida* (biotype B), *P. putida* (arvilla) mt-2, *P. putida* (119), *P. aeruginosa, P. fluorescens, P. desmolyticum, P. rhodochrous, P. mildenbergil, Pseudomonas sp.* (NCIB9816), *Pseudomonas sp.* (53/1), *Pseudornonas sp.* (53/2), *Aeromonas sp., Moraxella sp., Beijerinckia sp., Flavobacterium sp., Achromobacter sp., Nocardia sp.,* and *Corynebacterium renale.*

4. Nutrient agents

Contaminant-reducing agents in accordance with the invention can also include nutrient agents. As used herein, the term "nutrient agent" is defined as any substance that accelerates degradation by stimulating the growth of a microbial agent, whether the microbial agent is impregnated in the superabsorbent polymer or not. Nutrient agents can be composed of macronutrients, micronutrients, or mixtures of both. Generally, the nutrient agents include carbon sources, nitrogen sources, phosphorous sources, or mixtures thereof. Examples of specific nutrient agents that can be used in accordance with the invention are the BI-CHEM ACCELERATOR series (available from Sybron Biochemicals Inc., Birmingham, N.J.). The nutrient agent employed will vary according to the particular microbial agent being used to control contaminants, as well as the environmental context of its application. In some cases, for example with certain starch graphed superabsorbent polymers, the polymer matrix itself can also serve as a nutrient agent for the microbial agent.

One embodiment of the invention includes the use of nutrient agents to enhance the activity of the microbial agent. Preferably, the nutrient agent and the microbial agent are both impregnated within the superabsorbent polymer to enhance bioremedial activity of the nutrient agent. The nutrient agent can be used alone with the superabsorbent polymers as well to enhance the bioremedial activity of nutrient agents occurring naturally in the environment, although this is not the preferred embodiment.

The superabsorbent solid organic polymers may be used in proximity to natural or applied microbial or nutrient contaminant-reducing agents. As used herein, the term "natural" means naturally-occurring in the sense that the contaminant-reducing agents are found in nature. The term "applied", when used in association with contaminant-reducing agents, means that the agent is supplied by some non-natural method, as by the use of superabsorbent polymers.

C. Controlled Release Contaminant-Reducing Agent Delivery Composition

The contaminant-reducing compositions of the present invention can be prepared by mixing, encapsulating, agglomerating, or formulating one or more of the contaminant-reducing agents with one or more superabsorbent polymers and optionally one or more non-toxic and inert adjuvants or diluents into compositions such as solid powders, dusts, granules, pellets, briquets, extrusions, laminates, or composites, or into sprayable, pumpable, or injectable, variable-viscosity water or oil-base formulations such as gels or semi-gels. These compositions can be optionally incorporated into water-soluble or biodegradable/degradable packets, pouches, or capsules, made of, for example, polyvinyl alcohol, hydroxypropyl methyl cellulose, polyethylene oxide, or gelatin, or insoluble devices made, for example, of polyethylene or polypropylene, for use as secondary delivery vehicles for contaminant-reducing compositions. Preferably, the weight ratio of superabsorbent polymer to the total amount of the contaminant reducing agent and any inert diluent ingredients in the composition is about 0.1:100 to about 100:0.001. Other ranges are useable in accordance with the invention, and the preferred ranges will vary according to the situation in which the composition is being used.

In particular, the present invention is directed toward a method of formulating one or more superabsorbent polymer (s) with one or more contaminant-reducing agents, with or without water or other additives, into compositions such as solid powders, dusts, granules, agglomerates, pellets, briquets, extrusions, laminates, or composites, or into sprayable, pumpable, or injectable, variable-viscosity water or oil base gel or semi-gel like formulations that can release one or more active ingredients to simultaneously or concurrently control a variety of inorganic or organic contaminants with a single or multiple application of a solid or liquid single or multi-product formulation. Preferably, the release occurs in a controlled manner.

Impregnation of superabsorbent polymers with fatty alcohol film-forming agents such as POE-2-isostearyl alcohol or sorbitan monooleate appear to delay or slow down the rate of water absorption of superabsorbent polymers such as SUPER SORB or WATER LOCK G-100, thereby providing another useful mechanism for slow or controlled release of contaminant-reducing agents.

The slow or controlled release process could be further modified or delayed by the degree of compaction of the powdered or flaked superabsorbent polymer and superabsorbent polymer/contaminant-reducing agent formulations, by varying the size of an orifice or the number of orifices in a container into which the formulation is placed, by varying the concentration of film-forming agent, by varying the concentration of different types of superabsorbent polymers, and by adding one or more binders. For example, using one or more cationic, anionic, or nonionic surfactants or surface active agents in the composition can regulate the rate and duration of delivery (i.e., increase or decrease) of the contaminant-reducing agent from the superabsorbent polymer matrix. Additionally, a coating can be utilized to alter the swelling potential of the superabsorbent polymer, and thereby slow the rate of release of the contaminant-reducing agent from the superabsorbent polymer matrix. The coating can be hydrophobic or have varying degrees of water solubility.

It should be noted that certain salts (e.g., alkali metal halides such as NaCl) have been shown to reduce the swelling of the superabsorbent polymer matrix when introduced into water. This can have an impact on the contaminant-reducing agent delivery composition's ability to swell and control the target contaminant. Therefore, it is possible to utilize certain salts in superabsorbent polymer-based compositions as another mechanism to adjust the controlled-release rate and controlled-release profile of the contaminant-reducing agents contained therein. The rate of release will be further modified by the salinity of the environment. For example, certain superabsorbent polymers swell less in sea water, so the rate of release is slower.

Preferably, the contaminant-reducing agent delivery composition of the present invention contains one or more nontoxic and inert adjuvants or diluents such as carriers, binders, coatings, defloculating agents, penetrants, spreading agents, surface-active agents, surfactants, suspending agents, wetting agents, stabilizing agents, compatibility agents, sticking agents, waxes, oils, co-solvents, coupling agents, foams, antifoaming agents, synthetic plastics, elastomers, synergists, natural or synthetic polymers, UV protectants, buoyancy modifying agents, biocides, and other additives and mixtures thereof. Some materials may be biodegradable, or photodegradable (e.g., ultraviolet light), and others may be degraded by hydrolysis.

For aquatic treatments of surface contaminants, a floating superabsorbent polymer-based, contaminant-reducing agent composition is preferred. Most superabsorbent polymers have a specific gravity greater than one, and therefore, will require a buoyancy material or device to keep the compositions of the present invention at or near the surface of the water especially when the superabsorbent polymers are hydrated. For example, low specific gravity materials such as cetyl alcohol, stearyl alcohol, myristyl alcohol, cork, styrofoam, polymers, plastics, hydrophobic silica or sawdust could be intimately mixed with or incorporated into the polymer matrix via admixing procedures with one or more superabsorbent polymers. Another embodiment utilizes floating containers (e.g., plastic or mesh bags) to carry and release the superabsorbent polymer-based, contaminant-reducing agents through one or more orifices, slots, etc., in proximity to the surface contaminant.

Surface-active compositions of the present invention could also be developed by mixing low specific gravity chemicals or materials directly with the monomers utilized in the polymerization process to fabricate a superabsorbent polymer that, when swollen, will float due to the low specific gravity/hydrophobic materials being integrally incorporated or grafted into the superabsorbent polymer matrix, thereby releasing contaminant-reducing agents having a specific gravity less than or greater than one, at or near the surface of the water.

Another embodiment may include the admixing and entrapment of gases such as nitrogen, air, or helium in the superabsorbent polymer or superabsorbent polymer compositions of the present invention to aid in floating. Furthermore, these gases may be incorporated, mixed or bubbled directly with the monomer ingredients utilized in the polymerization process, and thereby create pockets of gases throughout the superabsorbent polymer matrix that will allow the matrix compositions of the present invention to remain at or near the surface of the water when hydrated and releasing the contaminant-reducing agent(s). Microbial and nutrient contaminant-reducing agents that have specific gravities greater than one will require surface orientation when used to control petroleum contaminants in aquatic habitats, particularly in deep water (e.g., ocean) environments.

The contaminant-reducing agent delivery composition can be applied to the contaminated site by conventional ground, aquatic or aerial techniques, including, but not limited to, perimeter application from the shore, application of the compositions via a spray boat, a boat equipped with a skimmer, surface ship, airboat, submarine, or application via fixed wing aircrafts, rotorcrafts or spray planes. In a terrestrial environment, the composition can be applied directly on the soil surface or mulched into the soil. In an aquatic environment, the composition should be applied at or near the surface of water. Preferably, the contaminant-reducing agent delivery composition is applied at a total bulk application rate of about 0.1 to about 2000 pounds per surface acre of the target environment. More preferably, the contaminant-reducing agent delivery composition is applied at a total bulk application rate of about 0.1 to about 500 pounds per surface acre of the target environment. The application range will depend upon the type of agent used, the particular superabsorbent polymer employed, the duration and rate of release desired, the total application rate required to uniformly treat the area of contamination, the type and concentration of contaminant, and the concentration of natural contaminant-reducing organisms and nutrients in the target habitat.

The invention will be further described by reference to the following detailed examples. These examples are offered to further illustrate the various specific and preferred embodiments and techniques. It should be understood, however, that many variations and modifications may be made while remaining within the scope of the present invention.

EXAMPLE 1

Five grams of a powdered 1:1 mixture of 75% sorbitan monooleate plus 25% 2-ethyl butanol and SUPER SORB superabsorbent polymer were dispensed on the surface of a body of water. Water in the areas contained visible iridescent residues of floating petroleum products, diesel No. 2, oils, and/or gasoline from the boats that were docked and had passed through the area. Wind speed at the time of the demonstration was less than 5 mph.

Some of the film-forming agent was released immediately upon contact with the water, producing a clear iridescent-free (i.e., petroleum-free) area as the film-forming agent formulation spread out in a concentric manner over the surface of the water while pushing and compacting the petroleum products outward from the point of application. The surface water around seven docks and a large portion of the entry canal were cleaned of petroleum residue within several minutes of application. Some of the petroleum products that were compacted along the seawall were removed with a mop, thereby demonstrating the use of the superabsorbent film-forming agent formulation for use in oil collection and dispersal.

EXAMPLE 2

Five grams of a powdered 1:1 mixture of 100% POE-2isostearyl alcohol and SUPER SORB superabsorbent polymer were dispensed on the surface of a body of water. Water in the areas contained visible iridescent residues of floating petroleum products, diesel No. 2, oils, and/or gasoline from the boats that were docked and had passed through the area. Wind speed at the time of the demonstration was less than 5 mph.

Some of the film-forming agent was released immediately upon contact with the water, producing a clear iridescent-free (i.e., petroleum-free) area as the film-forming agent formulation spread out in a concentric manner over the surface of the water while pushing and compacting the petroleum products outward from the point of application. The surface water around seven docks and a large portion of the entry canal were cleaned of petroleum residue within several minutes of application. Some of the petroleum products that were compacted along the seawall were removed with a mop, thereby demonstrating the use of the superabsorbent film-forming agent formulation for use in oil collection and dispersal.

EXAMPLE 3

A series of bioremediation bioassays were conducted in three water qualities to evaluate the efficacy of granular controlled delivery contaminant-reducing microbial compositions composed of a starch grafted sodium polyacrylate superabsorbent polymer matrix (SANWET IM-1500 LP), an acrylic acid, co-polymer release-rate regulator (PEMULEN TR-1; The B.F. Goodrich Company, Cleveland, Ohio) and a petroleum-degrading bacterial formulation (ABR Diesel Blend of viable bacterial cultures on a wheat bran base; code: 9577; Sybron Chemicals Inc., Palm Harbor, Fla.), in reducing the amount of aquatic contamination of No. 2 diesel fuel. Superabsorbent polymer granules were loaded in an aqueous formulation of bacterial and release rate regulator according to the following microsponging and entrapment procedure: 0.375 g (0.1% w/w) PEMULEN TR-1 was added to 337.12 g (89.9% w/w) water purified by reverse osmosis filtration (RO) in 500 ml NALGENE bottles and vigorously mixed on a STROKEMASTER paint shaker for approximately 30 minutes. Next, 37.5 g (10% w/w) ABR Diesel Blend was then added to the aqueous formulation and mixing was continued for an additional 60 minutes. Subsequently, 5.0 g (w/w) SANWET IM-1500 LP superabsorbent polymer granules were then added into the aqueous bacterial formulation and mixed for an additional 30 minutes to load the granules with the aqueous formulation ingredients. Swollen (hydrated) granules containing the formulation ingredients were rinsed with approximately 1000 ml RO water on a 10 mesh sieve to remove excess coating. Swollen granules were dried in a low-humidity room maintained at approximately 27–38% relative humidity (RH) and 24–26° C. for 96 hours. Dry, dehydrated granules were placed into 40 ml glass vials and stored until use. Granule composition was approximately 59.0% (w/w) ABR Diesel Blend, 0.6% (w/w) PEMULEN TR-1, and 40.4% (w/w) SANWET IM-1500 LP superabsorbent polymer.

EXAMPLE 4

Granular controlled release SANWET IM-1500 LP superabsorbent polymer-base nutrient compositions utilized in conjunction with the bacterial composition of Example 3 consisted of a balanced blend of nitrogen, phosphorus, and micronutrients (BI-CHEM Accelerator II Special; code: 9546; Sybron Chemicals Inc., Palm Harbor, Fla.) and a release-rate regulator (PEMULEN TR-1). Superabsorbent polymer granules were loaded in an aqueous formulation of nutrients and a release-rate regulator ingredients. The following microsponging and entrapment procedure was utilized to formulate controlled delivery granules for bioassay: 0.375 g (0.1% w/w) PEMULEN TR-1 was added to 337.12 g (89.9% w/w) water purified by reverse osmosis filtration (RO) in 500 ml NALGENE bottles and vigorously mixed on a STROKEMASTER paint shaker for approximately 30 minutes. Further, 37.5 g (10% w/w) BI-CHEM Accelerator II Special was then added to the aqueous formulation and mixed for an additional 60 minutes. Next, 5 g (w/w) SANWET IM1500 LP superabsorbent polymer granules were then added to the water-base nutrient formulation. Swollen (hydrated) granules were rinsed with approximately 1000 ml RO to remove excess coating. Swollen granules were dried in a low-humidity room at approximately 27–38% relative humidity and 24°–26° C. for 96 hours. Dry, dehydrated granules were placed into 40 ml glass vials for storage until use. Granule composition was approximately 62.1% (w/w) BI-CHEM Accelerator II Special, 0.6% (w/w) PEMULEN TR-1, and 37.3% (w/w) SANWET IM-1500 LP superabsorbent polymer.

EXAMPLE 5

A series of comparative bioremediation granule-transfer bioassays were conducted to determine the efficacy of controlled delivery superabsorbent polymer-based granular formulations composed of contaminant-degrading bacterial microorganisms and nutrients in reducing the level of petroleum contaminants in aquatic habitats having three types of water quality. The target petroleum contaminant was No. 2 diesel fuel.

Granular compositions fabricated in Examples 3 and 4 were utilized in the aquatic bioassays. Tests were conducted in fresh water (RO), 50% seawater (INSTANT OCEAN), and 100% seawater (INSTANT OCEAN). Tests were replicated three times.

The following bioassay protocol was utilized: 487.5 g of RO water, 50% seawater or 100% seawater was added to PYREX or KIMAX crystallizing dishes (125×65 mm). Depth of the water was approximately 45 mm. Next, 12.5 g No. 2 diesel fuel (approximately 25,000 ppm) was pipetted on the surface of the water (487.5 g) of each water quality series. The No. 2 diesel fuel layer at the surface of the water was approximately 3 mm thick. In order to assure that a sufficient nutrient base was established to support microbial growth 3 g of BI-CHEM Accelerator II Special was preapplied to each water quality.

Two granular application rates for each bacterial and nutrient composition were evaluated in the 3 water qualities containing the petroleum contaminant. Rates were applied to achieve bacterial levels of approximately $10^5$–$10^6$ cfu (colony forming units)/ml. A low granular application rate consisted of applying 0.35 g (approximately 292 granules at 0.0012 g/granule) of SANWET IM-1500 LP superabsorbent polymer granules loaded with ABR Diesel Blend (i.e., 0.2 g ABR Diesel bacterial cultures) and 0.65 g (approximately 342 granules at 0.0019 g/granule) of SANWET IM-1500 LP superabsorbent polymer granules loaded with BI-CHEM Accelerator II Special nutrient complex to the surface of each crystallizing dish containing 25,000 ppm No. 2 diesel fuel on RO, 50% seawater, and 100% seawater. At this application rate, controlled delivery ABR Diesel bacteria granules contained approximately $2\times10^6$ cfu/ml when applied to the petroleum-contaminated aquatic habitats.

A high granular application rate consisted of applying 0.70 g (approximately 584 granules at 0.0012 g/granule) of SANWET IM-1500 LP superabsorbent polymer granules loaded with ABR Diesel Blend (i.e., 0.4 g ABR Diesel bacterial cultures) and 1.3 g (approximately 684 granules) of SANWET IM-1500 LP superabsorbent polymers loaded with BI-CHEM Accelerator II Special nutrient complex to the surface of each crystallizing dish containing 25,000 ppm No. 2 diesel fuel on RO, 50% seawater, and 100% seawater. At this application rate, controlled delivery ABR Diesel bacteria granules contained approximately $4\times10^6$ cfu/ml when applied to the petroleum-contaminated aquatic habitats.

Technical non-superabsorbent polymer standards containing 25,000 ppm No. 2 diesel fuel and 0.1 g ($1\times10^6$ cfu/ml) ABR Diesel Blend and 3 g BI-CHEM Accelerator II Special were also prepared in each of the 3 water qualities. Higher total levels of the bacteria blend were loaded into the granular compositions, since they were expected to release low levels of the bacterial cultures according to square-root-of-time or first-order kinetics for prolonged periods after an initial "burst" effect. Controls contained diesel-contaminated water and no bacteria.

To assure maintenance of aerobic conditions in each water quality, water was initially aerated via an aquarium air pump and plastic tube for 0.5 minutes every three days, and then on a daily basis for 0.5 minutes for RO water, 1 minute for 50% seawater, and 1.5 minutes for 100% seawater due to differences in dissolved oxygen levels. Water levels were maintained at 1–2 day intervals. Bioassay room temperature and humidity ranged from 26°–28° C. and 76–86% relative humidity, respectively. Comparative biodegradation of the No. 2 diesel in all water qualities at each application rate was evaluated on a qualitative and/or quantitative basis.

Duration of effective controlled delivery of satisfactory concentrations of ABR Diesel Blend bacterial cultures and BI-CHEM Accelerator II Special was determined by transferring the hydrated bacteria and nutrient loaded granules to new test chambers (i.e., crystallizing dishes) containing new water and No. 2 diesel fuel, and evaluating the rate and duration of biodegradation of the diesel resulting from the release of bacteria from the granules. Comparative qualitative evaluations were based on the visual degradation (i.e., emulsification and reduction in size) of the surface layer of the No. 2 diesel fuel in all water quantities on a daily basis. Quantitative evaluations were based on diesel degradation in the high bacterial and nutrient application rate. Comparative post-treatment analyses of the concentration of diesel in tests and controls were only conducted in 100% seawater. Analyses of the average Total Petroleum Hydrocarbons (TPH) at various posttreatment intervals were conducted in pooled samples of the 3 water qualities according to EPA protocol 418.1 (Sybron Chemicals Inc.). At these posttreatment periods, the bacterial and nutrient granules were removed from each water quality, rinsed through a basket strainer, and transferred to new test chambers containing 495.0 g of RO, 50% seawater, or 100% seawater, 3 g BI-CHEM Accelerator II Special, and 5 g No. 2 Diesel fuel (i.e., 10,000 ppm). A series of granule transfers were evaluated (e.g., Transfers #1, 2, and 3).

Visual observations of the petroleum layer indicated a gradual emulsification/gellying and reduction in the size of the layer of No. 2 diesel fuel when compared to controls. The rate of biodegradation appeared to be slightly faster in the standards when compared to the superabsorbent polymer granular compositions; however, this was attributed to the lower level of free bacterial cultures initially present in the water column due to the slow rate of release of the bacterial from the superabsorbent polymer granules. Similar visual signs of biodegradation of the No. 2 diesel fuel layer were recorded in all granule transfer tests. Comparative observations indicated that the speed of degradation was directly related to the application rates of the loaded superabsorbent polymer granules, i.e., degradation of the diesel layer appeared to be about twice as fast in tests at the high bacterial and nutrient rates when compared to tests conducted at the lower rates.

Quantitative analysis of tests containing superabsorbent polymer-based compositions containing approximately $4\times10^6$ cfu/ml at 21 days post-treatment resulted in average TPH levels of approximately 7740, 6110, and 4750 mg/l for RO, 50% seawater, and 100% seawater tests, respectively. The average TPH in the standard containing 100% seawater was 3780 mg/l . The average control TPH levels was 23,880–24,360 mg/l.

IM-1500 LP Superabsorbent Polymer-base bacteria and nutrient granules transferred from the 25,000 ppm diesel-contaminated water qualities at 21-days posttreatment to the 10,000 ppm No. 2 diesel fuel water qualities were observed to be effective in slowly degrading the petroleum-contaminant in the 3 water qualities. Emulsification of the diesel layer resulting in a gellying and reduction in the diameter of the surface layer of diesel was observed to slowly increase over the initial 21-day test period. A second series of analyses (Transfer #1) of the diesel contamination in the 3 water qualities treated with the controlled delivery superabsorbent polymer-base bacterial and nutrient granular compositions at 19 days posttransfer (i.e., 40 days posttreatment) resulted in average TPH levels of 7100, 455, and 488 mg/l in RO, 50% seawater, and 100% seawater tests, respectively. The TPH levels in the controls were 9,810–10,080 mg/l . Similar visual signs of biodegradation of the diesel layer were observed over the 19 day posttransfer period in the 3 water qualities.

It should be noted that visual observations of the third transfer at 14 days post-transfer of the superabsorbent polymer granules (i.e., 54 days posttreatment) containing the bacterial and nutrients to new diesel-contaminated (i.e., 10,000 ppm) water (RO, 50% seawater, and 100% seawater) indicated that the rate of biodegradation of the surface layer of diesel was comparable to the second transfer. Granules were still active when the tests were terminated, suggesting that the starch-grafted superabsorbent polymer granules were still effective in releasing satisfactory levels of the diesel-degrading bacterial and nutrients for a prolonged period. In addition, it was possible that the starch-based granules also served as "mini-fermenters" for regenerating bacteria within the starch-grafted matrix for slow-release into the water. Different degrees of biodegradation of the granules were observed in the transfers.

Different amounts of nutrients (i.e., BI-CHEM Acceleration II Special) were observed in the hydrated superabsorbent polymers granules exposed to the 3 water qualities containing the 25,000 or 10,000 ppm diesel contaminants. For the most part, observed nutrient concentrations in the granule (i.e., based on color differences) appeared to follow the trend 100% seawater>50% seawater>RO water. This suggested that nutrient release rates from the superabsorbent polymer granules increased with decreasing salinity.

In general, results of bioassays indicated that superabsorbent polymer granules can be used as matrices for the prolonged controlled release of bacteria and nutrients used for bioremediation of petroleum contaminants in aquatic environments having a variety of water qualities. Controlled release of the contaminant-reducing agents appeared to be via a swelling controlled diffusion process and gradual biodegradation of the superabsorbent polymer matrices. The rate of petroleum biodegradation was directly related to the application rate of bacteria and nutrient granules. Bioassay results further suggested that the dense controlled-release granular compositions would produce petroleum contaminant-reducing efficacy in shallow water, but would be required to float at or near the surface of the water to deliver the contaminant-reducing agent(s) in proximity to the surface contaminant in deep water habitats such as oceans. Results also suggested that the starch-grafted superabsorbent polymer granules may serve as a nutrient source for regeneration of the bacteria for prolonged controlled release.

EXAMPLE 6

A series of terrestrial bioremediation bioassays were conducted in soil to evaluate the efficacy of powdered controlled delivery admixture formulations composed of a starch-g-poly(2-propenamide-co-2-propanoic acid, sodium salt) superabsorbent polymer (WATER LOCK A-140), a No. 2 diesel fuel-biodegrading bacterial formulation (i.e., ABR Diesel Blend of viable bacterial cultures on a wheat bran base; code: 9577), and a nutrient blend (i.e., BI-CHEM Accelerator II Special; code: 9546) in reducing the levels of a petroleum contaminant on land. The target contaminant utilized in these terrestrial bioremediation bioassays was No. 2 diesel fuel (i.e., 25,000 ppm/petri dish habitat). Tests were conducted in uncontaminated field collected soil used for fill at the Lee County Mosquito Control District. Tests were replicated 3 times.

The following protocol was utilized to prepare the experimental contaminated habitats: 26.25 g (2.5% w/w) No. 2 diesel fuel was slowly admixed with 1023.75 g (97.5% w/w) moist soil in a stainless steel bowl with a KITCHENAID KSM 90 mixer (No. 2 speed; flat beater blade) for approximately 5 minutes. Comparative bioassays were conducted with superabsorbent and non-superabsorbent polymer-base compositions.

In the protocol for superabsorbent polymer-base compositions, a premixed (5 minutes) formulation of 0.07 g (0.01% w/w) ABR Diesel Blend of viable bacterial cultures on a wheat bran base (code: 9577), 12.60 g (1.15% w/w) BI-CHEM Accelerator II Special nutrient blend (code: 9546), and 12.67 g (1.15% w/w) superabsorbent polymer powder (WATER LOCK A-140) was thoroughly blended into the diesel-contaminated soil with a KITCHENAID KSM 90 mixer for approximately 7 minutes to achieve a homogeneous mixture of the components. Next, 153.62 g of this superabsorbent polymer/soil composition was added to each 100×15 mm glass petri dishes and lightly hand-compacted to level the soil-controlled release admixture. Throughout the soil surface and subsurface, 5 ml RO water was pipetted to provide a moist soil environment and swollen superabsorbent polymer matrices of bacteria and nutrients throughout the soil. The soil was remoistened with 5 ml RO water at 3-day intervals and aerated by turning the soil with a spatula and re-leveled at 1-3 day intervals. Each petri dish in this series contained approximately $1\times10^5$ cfu/g soil (approximately 0.01 g ABR Diesel bacteria cultures on a wheat bran base), 1.80 g BI-CHEM Accelerator II Special nutrient complex, 1.81 g WATER LOCK A-140 superabsorbent polymer powder, and 3.75 g (i.e., 25,000 ppm) No. 2 diesel fuel.

Bioassays were also conducted with a standard non-superabsorbent polymer-base powdered admixture composition. In this protocol, a premixed (5 minutes) formulation 12.60 g (1.19% w/w) of BI-CHEM Accelerator II Special (code: 9546) and 0.07 g (0.01% w/w) ABR Diesel Blend of viable bacterial cultures on a wheat bran base (Code 9577) was thoroughly blended into the 1023.75 g (96.3% w/w) of soil and 26.25 g (2.5% w/w) No. 2 diesel fuel (25,000 ppm) admixture with a KITCHENAID KSM 90 mixer for approximately 5 minutes to assure a homogeneous mixture of all components. Next, 153.62 g of the non-superabsorbent polymer-base mixture was added to each 100×15 mm glass petri dish and lightly hand-compacted to level the composition. Each petri dish in this series contained approximately $1\times10^5$ cfu/g of soil (approximately 0.01 g ABR Diesel Blend of bacteria), 1.8 g BI-CHEM Accelerator II Special nutrient blend and 3.75 g No. 2 diesel fuel (25,000 ppm).

Subsequently, 5 ml RO water was pipetted throughout the soil surface and subsurface to provide a moist environment and swollen superabsorbent polymer matrices of bacteria and nutrients throughout the soil. The soil was remoistened with 5 ml RO water at 3-day intervals and aerated with a spatula and releveled at 1-3 day intervals. Controls contained 146.25 g moist soil and 3.75 g No. 2 diesel fuel.

Bioassay room temperature and humidity ranged from 26°–33° C. and 74–86% relative humidity, respectively. Biodegradation of the No. 2 diesel fuel in soil with the superabsorbent polymer and non-superabsorbent polymer-base powdered compositions was evaluated on a quantitative basis. Effectiveness of the petroleum-reducing, controlled release powdered formulation of ABR Diesel Blend bacteria, BI-CHEM Accelerator II Special nutrient blend, and WATER LOCK A-140 superabsorbent polymer matrices in biodegrading the No. 2 diesel contaminated throughout the soil was based on quantitative analyses of the concentration (mg/kg) of Total Petroleum Hydrocarbons (TPH) of pooled soil subsamples at various posttreatment intervals (EPA test SW-846 9071; Sybron Chemicals Inc.). This data was compared to the TPH levels in non-superabsorbent polymer standards and controls.

Duration of effective controlled delivery of satisfactory concentrations of bacteria and nutrients from the WATER LOCK A-140 superabsorbent polymer matrices throughout the soil was determined by transferring at 21 days posttreatment (Transfer #1) one-half of each superabsorbent polymer-base and non-superabsorbent polymer-base replicate (i.e., 75 g) containing the remaining (i.e., partially biodegraded) diesel-contaminated soil and nutrient/ABR Diesel Blend to new glass petri dishes containing an equivalent amount of clean soil (i.e., 75 g), 1.5 g (10,000 ppm) No. 2 diesel fuel, and 1.8 g nutrients (BI-CHEM Accelerator II Special). All components were blended together with a KITCHENAID KSM 90 mixer for approximately 5 minutes to assure a homogeneous mixture before being transferred into the new test chambers.

TPH analyses of soil containing No. diesel fuel (25,000 mg/kg), and a superabsorbent polymer-base (i.e., WATER LOCK A-140) ABR Diesel Blend and BI-CHEM Accelerator II Special powdered composition resulted in an average TPH level of 10,400 mg/kg at 21 days posttreatment. At this time period, approximately 58% of the No. 2 diesel fuel was biodegraded by the ABR Diesel Blend. Diesel-contaminated soil treated with the non-superabsorbent polymer-base composition (i.e., the standard) contained an average TPH level of 11,300 mg/kg, or a diesel No. 2 reduction of approximately 55%. These results indicated that the increased biodegradation efficacy observed with the superabsorbent polymer-base bacteria and nutrient compositions was due to the slower rate of evaporation that would be expected from water entrapped within the superabsorbent polymer matrices within the soil, when compared to non-encapsulated or free water within the soil. The higher degree of soil moisture was presumed to provide a more optimal environment for bacterial growth. Perhaps the starch portion of the superabsorbent polymer-base controlled delivery composition also added an additional nutrient source for increased bacterial growth.

Analyses of the controlled delivery superabsorbent polymer-base soil composition that was transferred at 21 days posttreatment (Transfer #1) to an admixture of nutrient-enriched soil contaminated with an additional 10,000 ppm No. 2 diesel fuel at 18 days posttransfer (i.e., at 39 days posttreatment) resulted in an average TPH concentration of 3780 mg/kg. Transfer of the non-superabsorbent polymer-base composition resulted in an average concentration of TPH of 4810 mg/kg. In general, results of comparative transfer bioassays indicated that the starch-grafted superabsorbent polymer matrices were effective in prolonging the release of entrapped petroleum-reducing bacteria and nutrients, while providing a more optimum soil moisture level and possible nutrient source for enhanced microbial activity.

EXAMPLE 7

A series of terrestrial bioremediation bioassays were conducted on sand to evaluate the efficacy of controlled delivery semi-viscous, liquid (i.e., water based) compositions of a starch-g-poly(2-propenamide-co-2-propanoic acid, potassium salt) superabsorbent polymer (WATER LOCK B-204) and a petroleum-degrading bacterial culture formulation (BIOTRACK DOL; code: 9690) in effectively reducing the level of surface petroleum contamination on land. The substrate utilized for this terrestrial bioassay series was TEXBLAST sand-blasting sand. The target contaminant was No. 2 diesel fuel.

The following protocol was utilized to prepare the experimental diesel-contaminated habitats for evaluating the superabsorbent polymer-base and non-superabsorbent polymer-base compositions of BIOTRACK DOL: 3.0 g No. 2 diesel fuel (i.e., 23,000 ppm) was squeeze-sprayed on the surface of 125 g sand in each 100×15 mm glass petri dish (3 replications/composition) with a 30 ml plastic drop-dispensing bottle. To evaluate the superabsorbent polymer-base compositions, 24.1 g premixed (KITCHENAID KSM 90 mixer) formulation of 3.5 g WATER LOCK B-204 and 165.2 g BIOTRACK DOL was uniformly pipetted over the surface of the diesel-contaminated sand. In bioassays with non-superabsorbent polymer-base standard compositions, 23.6 g of BIOTRACK DOL formulation was uniformly pipetted over the surface of the diesel-contaminated sand. Subsequently, 5 ml of RO water was applied to each experimental habitat containing the superabsorbent polymer-base and non-superabsorbent polymer-base formulations at 3-day intervals to assure that each habitat would have adequate moisture for bacterial growth. A control series contained 125 g sand that was surface-coated with 3 g No. 2 diesel fuel (i.e., 23,000 ppm).

Bioassay room temperature and humidity ranged from 26–33° C. and 74–86% relative humidity, respectively. Biodegradation of the No. 2 diesel fuel on the surface of the sand with the superabsorbent polymer-base and non-superabsorbent polymer-baseformulations was evaluated on a quantitative basis. Effectiveness of the petroleum-reducing controlled delivery, variable-viscosity formulation of BIOTRACK DOL bacterial composition and WATER LOCK B-204 superabsorbent polymer matrices in biodegrading the No. 2 diesel fuel contaminated on the surface of the sand was based on analyses of the concentration Total Petroleum Hydrocarbons (TPH) of sand subsamples at 21 days post-treatment. This data was compared to the concentration of TPH in non-superabsorbent polymer-base standards and controls.

Duration of effective controlled delivery of satisfactory levels of petroleum-degrading bacteria from the WATER LOCK B-204 superabsorbent polymer matrices on the No. 2 diesel-contaminated soil surface was determined by transferring at 21 days posttreatment one half of each superabsorbent polymer-base and non-superabsorbent polymer-based replicate (i.e., 75 g) containing the remaining (i.e., partially biodegraded) diesel-contaminated sand and BIOTRACK DOL to the surface of the sand in new glass petri dishes containing an equivalent amount of clean sand (i.e., 75 g) that was surface-coated with 1.25 g No. 2 diesel fuel (i.e., 10,000 ppm).

TPH analyses of the sand containing No. 2 diesel fuel (23,000 ppm) and a single application of a superabsorbent polymer-base (i.e., WATER LOCK B-204) BIOTRACK DOL formulation resulted in an average concentration of TPH of 12,600 mg/kg at 21 days posttreatment, or approximately 45% biodegradation of the No. 2 diesel fuel. Analyses of the diesel-contaminated sand treated with a single application of the standard non-superabsorbent polymer-base formulation resulted in a concentration of TPH of greater than 23,000 mg/kg at 21 days posttreatment, or virtually no biodegradation of the No. 2 diesel fuel. These results indicated that a significant increase in biodegradation efficacy observed with the superabsorbent polymer-base bacterial formulation was due to the increased amount of water at the surface area of the diesel contamination caused by the entrapment of water by the superabsorbent polymer. Water applied to surface of non-superabsorbent polymer formulations did not accumulate at the site of surface contamination, and therefore did not provide the bacteria with a sufficient source of moisture for adequate microbial growth for biodegradation of the No. 2 diesel. Water was observed to accumulate at the bottom of the petri dish in non-superabsorbent polymer tests, while swollen superabsorbent polymer matrices were observed at the sand surface, with no water accumulation being observed at the bottom of the petri dishes in tests with superabsorbent polymer-base formulations. Also, perhaps, the starch portion of the superabsorbent polymer matrices also provided an additional nutrient source for increased bacterial growth. In general, results of comparative bioassays with water-base superabsorbent polymer-base and non-superabsorbent polymer-base formulations clearly indicated that the starch-grafted superabsorbent polymer-base BIOTRACK DOL formulation was significantly more effective in reducing the level of surface petroleum contamination on sand when compared to a standard BIOTRACK DOL water-base formulation containing no superabsorbent polymer.

EXAMPLE 8

Three different superabsorbent polymers were formulated with a film-forming or bacterial contaminant-reducing agent and inert controlled release-rate regulator ingredients to evaluate the effect of superabsorbent polymer type and inert formulation components on the concentration of active contaminant-reducing agent loaded into the granules, and the profile of release of the components from the granules into an aquatic habitat. Superabsorbent polymer granules utilized in these evaluations were a potassium polyacrylate, lightly crosslinked (ARIDALL 11250), a starch grafted sodium polyacrylate (SANWET IM1500 LP), a partial sodium salt of a crosslinked polypropenoic acid (Dow XU 40346.00 Super Absorbent Polymer), a poly (sodium acrylate) homopolymer (SS Superabsorbent Polymer), a crosslinked polyacrylamide copolymer (ALCOSORB AB3C), a crosslinked potassium/polyacrylamide copolymer (STOCKOSORB 310 K), or a copolymer of acrylamide and sodium acrylate (AQUASORB PR-3005). Release-rate regulators included inert formulating materials that can retard or accelerate the rate of delivery or diffusion of the active contaminant-reducing agent(s) from the superabsorbent polymer granules, depending on the propensity of the active agents to leach from or be bound within the polymer matrices. Several nutrient formulations with no release-rate regulators were also evaluated. Non-limiting examples of release-rate regulators utilized in the admixtures included activated carbon (UCAR Carbon Co., Inc), hydrophilic silica (DEGUSSA FK 500 LS), acrylic acid copolymers (PEMULEN TR-1 or PEMULEN TR-2), sulfonated surfactants (sodium di-isopropyl naphthalene sulfonate: MORWET IP Powder; sodium mono and di-methyl naphthalene sulfonate: MORWET M Powder; or sodium alkyl aryl sulfonate: MORWET 3008 Powder), or a fatty alcohol polyethylene glycol ether (MARLIPAL 1618/25 P6000 powder). Contaminant-reducing agents included in the formulations were nutrient complexes (BI-CHEM Accelerator II Special), bacteria cultures that were unfiltered or filtered to remove large bran particles (ABR Diesel Blend; code: 9577 or ABR Gasoline Blend; code: 9350), or film-forming agents (sorbitan monooleate or a mixture of 75% sorbitan monooleate/25% 2-ethyl butanol). Microsponging and entrapment techniques were used to load the active and inert components in an aqueous medium into the superabsorbent polymers according to a 0.5, 1, or 3 hour aqueous admixing procedure (i.e., depending on the swelling potential the superabsorbent polymer granules) that is generally described in Example 4. The loading rates that were observed when superabsorbent polymer granules were admixed with an aqueous formulation of 10% contaminant-reducing agent and 1–10% inert formulation components (i.e.,1% MORWET products, 0.5% carbon and 0.1% silica for sorbitan monooleate-base compositions; or 10% MORWET or MARLIPAL products or 0.1% PEMULEN TR-1 for BI-CHEM Accelerator II nutrient compositions; or 0.1% PEMULEN TR-1 or TR-2 for ABR Gasoline Blend bacteria cultures; or 0.1% PEMULEN TR-1 for ABR Diesel Blend bacteria cultures) were as follows:

Film-Forming Agent (Henkel Corporation): Granule Compositions (% w/w):

31.2% sorbitan monooleate + 3.1% MORWET M + 1.6% carbon + 0.3% silica + 63.8% ARIDALL 11250.

30.0% sorbitan monooleate + 3.0% MORWET IP + 1.5% carbon + 0.3% silica + 65.2% ARIDALL 11250.

29.0% sorbitan monooleate/2-ethyl butanol + 2.9% MORWET M + 1.5% carbon + 0.3% silica + 66.3% ARIDALL 11250.

30.1% sorbitan monooleate/2-ethyl butanol + 3.0% MORWET IP + 1.5% carbon + 0.3% silica + 65.1% ARIDALL 11250.

33.7% sorbitan monooleate + 3.4% MORWET M + 1.7% carbon + 0.3% silica + 60.9% SANWET IM-1500 LP.

34.0% sorbitan monooleate + 3.4% MORWET IP + 1.7% carbon + 0.3% silica + 60.6% SANWET IM-1500 LP.

27.0% sorbitan monooleate/2-ethyl butanol + 2.7% MORWET M + 1.3% carbon + 0.3% silica + 68.7% SANWET IM-1500 LP.

28.5% sorbitan monooleate/2-ethyl butanol + 2.9% MORWET IP + 1.4% carbon + 0.3% silica + 66.9% SANWET IM-1500 LP.

13.2% sorbitan monooleate + 1.4% MORWET M + 0.7% carbon + 0.1% carbon + 0.1% silica + 84.6% XU 40346.00.

15.6% sorbitan monooleate + 1.6% MORWET IP + 0.7% carbon + 0.2% silica + 81.9% XU 40346.00.

10.2% sorbitan monooleate/2-ethyl butanol + 1.0% MORWET M + 0.5% carbon + 0.1% silica + 88.2% XU 40346.00.

12.2% sorbitan monooleate/2-ethyl butanol + 1.2% MORET IP + 0.6% carbon + 0.1% silica + 85.9% XU 40346.00.

Nutrient Agent (Sybron Chemical Inc.): Granule Compositions (% w/w):

39.6% BI-CHEM Accelerator II Special + 39.6% MORWET 3008 + 20.8% ARIDALL 11250.

39.0% BI-CHEM Accelerator II Special + 39.0% MORWET M + 22.0% ARIDALL 11250.

39.1% BI-CHEM Accelerator II Special + 39.1% MARLIPAL 1618/25 P6000 + 39.1% ARIDALL 11250.

39.3% BI-CHEM Accelerator II Special + 39.3% MORWET 3008 + 21.4% SANWET IM-1500 LP.

38.9% BI-CHEM Accelerator II Special + 38.9% MORWET M + 22.2% SANWET IM-1500 LP.

38.7% BI-CHEM Accelerator II Special + 38.7% MARLIPAL 1618/25 P6000 + 22.6% SANWET IM-1500 LP.

33.8% BI-CHEM Accelerator II Special + 33.8% MORWET 3008 + 32.4% XU 40346.00.

32.2% BI-CHEM Accelerator II Special + 32.2% MORWET M + 35.6% XU 40346.00.

31.7% BI-CHEM Accelerator II Special + 31.7% MARLIPAL 1618/25 P6000 + 36.6% XU 40346.00.

33.1% BI-CHEM Accelerator II Special + 33.1% MORWET 3008 + 33.8% STOCKOSORB 310K.

33.4% BI-CHEM Accelerator II Special + 33.4% MORWET M and 33.2% STOCKOSORB 310K.

26.5% BI-CHEM Accelerator II Special + 26.5% MARLIPAL 1618/25 P 6000 + 47% STOCKOSORB 310K.

31.1% BI-CHEM Accelerator II Special + 31.1% MORWET 3008 + 37.8% AQUASORB PR-3005.

31.1% BI-CHEM Accelerator II Special + 31.1% MORWET M + 37.8% AQUASORB PR-3005.

24.7% BI-CHEM Accelerator II Special + 24.7% MARLIPAL 1618/25 P6000 + 50.6% AQUASORB PR-3005.

39.6% BI-CHEM Accelerator II Special + 39.6% MORWET 3008 + 20.8% SS Superabsorbent Polymer.

38.3% BI-CHEM Accelerator II Special + 38.3% MORWET M + 23.4% SS Superabsorbent Polymer.

57.3% BI-CHEM Accelerator II Special + 0.6% PEMULEN TR-1 + 42.1% ARIDALL 11250.

62.1% BI-CHEM Accelerator II Special + 0.6% PEMULEN TR-1 + 37.3% SANWET IM-1500 LP.

45.4% BI-CHEM Accelerator II Special + 0.5% PEMULEN TR-1 + 54.1% XU 40346.00.

53.6% BI-CHEM Accelerator II Special + 0.5% PEMULEN TR-1 + 45.9% STOCKOSORB 310K.

44.9% BI-CHEM Accelerator II Special + 0.5% PEMULEN TR-1 + 54.6% AQUASORB PR-3005.

77.7% BI-CHEM Accelerator II Special + 22.3% SS Superabsorbent Polymer.

71.3% BI-CHEM Accelerator II Special + 28.7% SAN-WET IM-1500 LP.

72.1% BI-CHEM Accelerator II Special + 27.9% ARID-ALL 11250.

61.0% BI-CHEM Accelerator II Special + 39.0% XU 40346.00.

59.2% BI-CHEM Accelerator II Special + 40.8% STOCKOSORB 310K.

50.5% BI-CHEM Accelerator II Special + 49.5% AQUA-SORB PR 3005.

Bacterial Agents (Sybron Chemicals Inc.): Granule Compositions (%w/w):

51.0% ABR Diesel Blend (unfiltered) + 0.5% PEMULEN TR-1 + 48.5% ARIDALL 11250.

59.0% ABR Diesel Blend (unfiltered) + 0.6% PEMULEN TR-1 + 40.4% SANWET IM-1500 LP.

37.6% ABR Diesel Blend (unfiltered) + 0.4% PEMULEN TR-1 + 62.0% XU 40346.00.

48.4% ABR Diesel Blend (unfiltered) + 0.5% PEMULEN TR-1 + 51.1% STOCKOSORB 310K.

48.2% ABR Diesel Blend (unfiltered) + 0.5% PEMULEN TR-1 + 51.3% AQUASORB PR-3005.

21.7% ABR Gasoline Blend (filtered) + 0.2% PEMULEN TR-2 + 78.1% ARIDALL 11250.

50.8% ABR Gasoline Blend (filtered) + 0.5% PEMULEN TR-1 + 48.7% SANWET IM-1500 LP.

58.0% ABR Gasoline Blend (filtered) + 0.6% PEMULEN TR-2 + 41.4% SANWET IM-1500 LP.

17.3% ABR Gasoline Blend (filtered) + 0.2% PEMULEN TR-1 + 82.5% XU 40346.00.

15.8% ABR Gasoline Blend (filtered) + 0.2% PEMULEN TR-2 + 84.0% XU 40346.00.

37.1% ABR Gasoline Blend (filtered) + 0.4% PEMULEN TR-1 + 62.5% STOCKOSORB 310K.

36.8% ABR Gasoline Blend (filtered) + 0.4% PEMULEN TR-2 + 62.8% STOCKOSORB 310K.

48.4% ABR Gasoline Blend (filtered) + 0.5% PEMULEN TR-1 + 51.1% AQUASORB PR 3005.

47.7% ABR Gasoline Blend (filtered) + 0.5% PEMULEN TR-2 + 51.8% AQUASORB PR 3005.

27.5% ABR Gasoline Blend (unfiltered) + 0.3% PEMULEN TR-1 + 72.2% ARIDALL 11250.

33.5% ABR Gasoline Blend (unfiltered) + 0.3% PEMULEN TR-2 + 66.2% ARIDALL 11250.

53.9% ABR Gasoline Blend (unfiltered) + 0.5% PEMULEN TR-1 + 45.6% SANWET IM-1500 LP.

58.0% ABR Gasoline Blend (unfiltered) + 0.6% PEMULEN TR-2 + 41.4% SANWET IM-1500 LP.

18.2% ABR Gasoline Blend (unfiltered) + 0.2% PEMULEN TR-1 + 81.6% XU 40346.00.

15.0% ABR Gasoline Blend (unfiltered) + 0.2% PEMULEN TR-2 + 84.8% XU 40346.00.

41.6% ABR Gasoline Blend (unfiltered) + 0.4% PEMULEN TR-1 + 58.0% STOCKOSORB 310K.

42.5% ABR Gasoline Blend (unfiltered) + 0.4% PEMULEN TR-2 + 57.1% STOCKOSORB 310K.

51.0% ABR Gasoline Blend (unfiltered) + 0.5% PEMULEN TR-1 + 48.5% AQUASORB PR-3005.

51.4% ABR Gasoline Blend (unfiltered) + 0.5% PEMULEN TR-2 + 48.1% AQUASORB PR 3005.

53.6% ABR Gasoline Blend (unfiltered) + 0.5% PEMULEN TR-1 + 45.9% ALCOSORB AB3C.

50.0% ABR Gasoline Blend (unfiltered) + 0.5% PEMULEN TR-2 + 49.5% ALCOSORB AB3C.

Results of formulation studies indicated that the concentration of film-forming and bacterial contaminant-reducing agents loaded into the superabsorbent polymer granules via an aqueous microsponging procedure was a function of the type of superabsorbent polymer and/or the inert release-rate regulators utilized in the admixtures. Release-rate regulators also functioned as loading-level regulators. A series of visual demonstrations were designed to evaluate the effect of the superabsorbent polymer and the release-rate regulators on the controlled release of the petroleum contaminant-reducing agents from the superabsorbent polymer granules.

Comparative pan (30 cm×30 cm) tests in 2000 ml of 100% seawater (INSTANT OCEAN) containing 5000 ppm 30 weight motor oil with several types of sorbitan monooleate or sorbitan monooleate/2-ethyl butanol-base superabsorbent polymer granules (1 g) that were suspended at the water surface in mesh bags from styrofoam floats indicated that the duration of compaction of oil against the pan wall at the opposite end of where a granular formulation was introduced (i.e., the film-forming agent pressure) varied with the type of polymer and/or the type/concentration of inert formulation ingredients. Similar tests with a variety of the bacterial-base and nutrient-base superabsorbent polymer granules were also conducted in 100% seawater. Results of these tests at 21 days posttreatment indicated that the rate of visual biodegradation (i.e., evaluated on the basis of emulsification and reduction in surface area of the petroleum slick) of 5000 ppm No. 2 diesel fuel or 87 octane gasoline from ABR Diesel Blend or ABR Gasoline Blend, respectively, and BI-CHEM Accelerator II Special released from the granules (2 g) in floating mesh bags varied with the type of superabsorbent polymer, and/or the type and concentration of release-rate regulators utilized in the granule compositions. Significant differences in the visual amounts of nutrients remaining in the superabsorbent polymer granules were observed at 21 days posttreatment between nutrient granules loaded with release-rate regulators when compared to nutrient granules containing no release-rate regulators.

EXAMPLE 9

Duration of controlled release of film-forming contaminant-reducing agents from floating agglomerated superabsorbent polymer-base compositions and devices was evaluated in 5 gallon plastic buckets containing 4 gallons of 100% seawater (INSTANT OCEAN) and/or in experimental fresh-water ponds (50×50 ft.) having a variety of natural vegetation and invertebrate and vertebrate organisms. Film-forming agents utilized in the tests were sorbitan monooleate, a mixture of 75% sorbitan monooleate/25% 2-ethyl butanol, or POE(2)isostearyl alcohol. WATER LOCK A-140 superabsorbent polymer was formulated in the agglomerated compositions used in the bioassays and field evaluations; however agglomerated compositions were also prepared using Water Lock A-100, A-120, SUPER SORB, FAVOR CA100, and AQUA KEEP J-500.

Agglomerated compositions of WATER LOCK A-140 and film-forming agents were prepared in the following manner: 100 g sorbitan monooleate, 75 g sorbitan monooleate/25 g 2-ethyl butanol, or 100 g POE(2) isostearyl alcohol were added to 300 g acetone in a stainless steel bowl and blended with a KITCHENAID KSM 90 mixer (wire whip attachment) for 5 minutes on #2 speed. While mixing, 100 g WATER LOCK A-140 superabsorbent polymer powder was slowly added into a film-forming agent. Mixing was continued until the acetone had been driven off and the powdered composition was essentially flowable (approximately 2–3 hours). Next, 15 g of powdered superabsorbent polymer/film-forming agent composition was tightly packed into preformed, water soluble 2 mil polyvinyl alcohol bags (MONOSOL 8000 Series) and heat sealed. The encapsulated compositions were cured in a room maintained at ca 27° C. and 80% relative humidity for approximately 96 hours before being transferred to a drying room maintained at approximately 27° C. and 27–38% relative humidity for an addition 96 hours. 30 or 40 mesh nylon netting was then tightly or loosely wrapped around each bag to allow for different degrees of water-activated superabsorbent polymer swelling or expansion. Tightly fitted bags measured approximately 38×51 mm while loose fitting mesh bags were approximately 76×102 mm. A small cork or plastic float was attached to each end of a mesh bag to assure that the agglomerated compositions would be in contact with and just below the surface of the water in proximity to a floating contaminant. Powdered superabsorbent polymer-base film-forming agent compositions were also agglomerated into briquets or disquets by hand compaction of the compositions at various pressure in plastic tissue embedding molds (PEEL-A-WAY) or in plastic petri dishes (approximately 35×10 mm). 1:1 powdered controlled delivery compositions of superabsorbent polymers and ABR Diesel Blend or ABR Gasoline Blend or ABR Hydrocarbon Blend or BI-CHEM Accelerator II Special, with or without one or more release-rate regulators, were agglomerated and optionally encapsulated within water-soluble polyvinyl alcohol bags, or hand compacted into briquets or disquets as described above. Similar powdered compositions containing joint or multiple combinations of products such as 1:1:1 or 1:1:1:1 admixtures of a superabsorbent polymer, an ABR bacterial culture, a nutrient complex, and/or film-forming agent were agglomerated into a variety of matrix forms. By aligning the floating or submerged compositions in various arrangements and combinations, e.g., in layers, in tandem, linked together in a chain-type configuration, etc., one or more contaminants could be simultaneously contained and/or controlled for prolonged periods. Granular controlled-release compositions could be utilized in the same fashion. These controlled-delivery compositions would also have significant applications for the control of surface or subsurface contaminants in terrestrial habitats. Procedures for admixing, curing, drying, and hardening of the compositions are described above and in the examples.

Results of tests in fresh water ponds (approximately 240–280 umhos/cm) dusted with talc (i.e., to visualize spreading of the film-forming agents) indicated that the controlled release rate of a film-forming agent from the tight mesh bag was slower than from the loose mesh bag. Duration of film-forming agent persistence (i.e., film pressure) was monitored with ADOL (oleyl alcohol) indicator oil. Daily water temperature was approximately 35° C. Mesh size also affected the rate of delivery by restricting or slowing the release of expanded superabsorbent polymer-base components into the water. Bioassay results in buckets containing 100% seawater indicated that release of the film-forming agents from the superabsorbent polymer compositions was significantly slower than observed in the fresh water due to the general inhibition of superabsorbent polymer swelling in high salinities. Similar trends in release due to mesh tightness and mesh size were also observed.

In general, these observations suggested that various devices could be fabricated that could regulate the rate of delivery of the contaminant-reducing or controlling agent by restricting the polymer swelling potential and/or surface area of the polymer in contact with the water, for example, by varying the size and number of openings or pores in a hollow, floating or submerged device. Further modification in release rate could be obtained by selecting superabsorbent polymers with different swelling and biodegradation parameters and/or by admixing various release-rate regulators ingredients into the formulation. Low pressure and high pressure compaction techniques and the use of various binders and hydrophobic or insoluble coatings could be further utilized to vary the release rate of the contaminant-reducing agents from the superabsorbent polymer matrices. These agglomerated formulations and devices could be applied to any single, joint, or multiple combination of microbial, nutrient, or film-forming agents used to control contaminants in water. Granular compositions could also be utilized in the above mentioned devices. These controlled-release compositions could also be utilized in terrestrial contaminant-controlling or reducing applications.

EXAMPLE 10

A series of tests were designed to evaluate the effectiveness of superabsorbent polymers alone (i.e., without the incorporation of a film-forming, microbial or nutrient contaminant-reducing agent) in controlling water-borne organic and inorganic contaminants in terrestrial environments by entrapping and concentrating the contaminants within the water-activated superabsorbent polymer matrix before significant vertical or horizontal leaching or migration could occur from the initial site of introduction. The organophosphate insecticide DURSBAN 4E (chlorpyrifos) was selected as an example of an organic pesticide contaminant while a series of metallic and non-metallic elements were selected as examples of inorganic contaminants. Copper metal (Cu,-325 mesh, 99.5% pure), aluminum metal (Al,-325 mesh, 99.5% pure), tin metal (Sn,-325 mesh 99.8% pure), zinc metal (Zn,-325 mesh, 99.8% pure), chromium metal (Cr,-325 mesh, 99.2% pure), iron metal (Fe,-325 mesh, 99.9% pure), and nickel-chromium metal (Ni—Cr,-225 mesh, 80–20 wt. %, 99.0% pure) were utilized as metallic elements (Cerrac, Inc.), while carbon and graphite fine powder (approximately-325 mesh) were utilized as non-metallic elements (UCAR Carbon Co., Inc.).

Tests were conducted in plastic cups (FABRI-KAL 16S) or 100×15 mm glass petri dishes containing 75 g or 50 g of soil for organic or inorganic contaminant evaluations, respectively. Two layers of SANWET IM-1500 Flake superabsorbent polymer (approximately 90 mm diameter; 3 g) were sandwiched between an upper and lower layer of nylon netting (30 or 40 mesh) that were joined around the perimeter with staples. The mesh covered double layer of superabsorbent polymer flakes were placed over the surface of the soil to serve as a water-activated protective barrier that could entrap water-borne organic or inorganic contaminants in a defined location, and thereby prevent spreading of the contaminant to areas far removed from the point(s) of initial introduction. Tests with inorganic and organic contaminants were replicated 3 times and conducted in a room maintained at approximately 27° C. and 80% relative humidity.

The following bioassay protocol was utilized to evaluate the efficacy of a removable superabsorbent polymer "mesh mat" in reducing the amount of a water-base DURSBAN 4E formulation (i.e., 0.25% chloropyrifos) from leaching into the soil, for example, as a result of a spill. In this test, 5 ml (5 g) of the 0.25% DURSBAN 4E formulation (0.25 g DURSBAN 4E + 99.75% distilled water) were pipetted over the surface of the superabsorbent polymer-covered soil in each plastic cup. Next, 5 ml of the insecticide solution was pipetted directly onto the soil in control groups having no superabsorbent polymer mat (i.e., screen mesh only—no SANWET IM-1500 flakes). To evaluate the pesticide entrapment potential of the superabsorbent polymer, bioassays against 10 German cockroaches (*Blattella germanica*) adults were conducted to evaluate the acute toxicity of the soil contaminated with the pesticide as a result of the application in mat-covered and uncovered soil (3 replications/test). The mesh with and without the superabsorbent polymer flakes were removed from the soil prior to introduction of the cockroaches. The weight of each plastic cup was then determined. Results indicated that a weight increase of 4.87, 4.83, and 4.89 g of water-base DURSBAN 4E was obtained in controls while no increase was obtained in the superabsorbent polymer-covered series. It is presumed that the slight reduction in pesticide solution in the soil of controls was due to a small amount of pesticide solution being retained on the double layer of nylon mesh. 100% of the cockroaches introduced on the soil having no superabsorbent polymer mat died within 24 hours post-introduction. No cockroach mortality was observed in tests containing the superabsorbent polymer mat.

The following test protocol was used to evaluate the efficacy of a removable superabsorbent polymer "mesh mat" in reducing the amount of water-borne metallic and non-metallic elements from leaching into the soil, for example, as a result of an industrial spill or run-off. In this test series, a metallic and non-metallic formulation of copper metal (0.5 g), aluminum metal (0.5 g), carbon (0.5%), graphite (0.5%), and distilled water (8.0 g), or a metallic formulation composed of copper metal (0.2857 g), aluminum metal (0.2857 g), tin metal (0.2857 g), zinc metal (0.2857 g), chromium metal (0.2857 g), iron metal (0.2857 g), nickel-chromium metal (0.2857 g), and distilled water (8.0 g) was applied from a plastic squeeze drop-dispensing bottle into glass petri dishes containing soil covered with a superabsorbent polymer mesh mat and soil that was not covered with a superabsorbent polymer mesh mat (control group—mesh only). An additional 2 g distilled water was added to the squeeze bottle after each application to wash any remaining metals/non-metals that were not dispensed in the application. Essentially 12 g of each water-base formulation was applied to test and control petri dishes (i.e., 2 g metallic/non-metallic contaminants + 10 g water carrier). The comparative efficacy of the superabsorbent polymer mat in reducing the amount of metallic/non-metallic contaminants in the soil was evaluated on a weight increase basis. Mesh with and without the superabsorbent polymer flakes were removed before weighing the petri dishes. The post-treatment weight increases of petri dishes containing soil that was covered with the superabsorbent polymer mat were 0.15, 0.07, and 0.16 g for the metallic/non-metallic formulation and 0.15, 0.12, and 0.12 g for the metallic formulation. Weight increases of petri dishes in controls were 11.87, 11.82, and 11.89 g for the metallic/non-metallic formulation and 11.83, 11.87, and 11.86 g for the metallic formulation. Observations indicated that a small residue of metals/non-metals and water was retained in the drop-dispensing bottles after each application.

In general, results of these tests indicated that superabsorbent polymers can be used to protect selected terrestrial habitats from being contaminated by certain organic and inorganic contaminants that are transported, carried or moved through/into the environment by water. Contaminant-entrapped superabsorbent polymers (e.g., mesh mats, laminates, etc.) can be removed from the surface or subsurface areas of placement and disposed of according to acceptable procedures. In some cases, the superabsorbent polymers can be washed to remove the contaminants and then reused in subsequent contaminant-controlling applications.

The complete disclosure of all publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A contaminant-reducing composition comprising a mixture of:
   (a) a contaminant-reducing agent comprising a microbial agent which effects bioremediation upon said contaminant, wherein said contaminant comprises a material selected from the group consisting of polycyclic aromatic hydrocarbons, polychlorinated biphenyls, organic solvents and oil
   (b) a superabsorbent hydrophilic solid acrylate or acrylamide organic polymer for delivery of the contaminant-reducing agent, said polymer being capable of absorbing over one hundred times its weight in water,
   wherein said composition is capable of reducing the amount of an organic contaminant in a 2000 ml sample comprising water by said microbial agent effecting bioremediation upon said contaminant in an environment where water is present in an amount sufficient to swell said organic polymer, and
   (c) at least one additional material selected from the class consisting of a film forming agent and a nutrient for said microbial agent.

2. The composition of claim 1 wherein said composition contains a film-forming agent which will increase the surface area of petroleum present in said water.

3. The composition of claim 1 wherein said composition when placed into a sample of water containing contaminant reduces the amount of contaminant in said 2000 ml sample of water, wherein said contaminant comprises pesticides.

4. The composition of claim 1 wherein said composition when placed into a sample of water containing contaminant reduces the amount of contaminant in said 2000 ml sample of water, wherein said contaminant is selected from the group consisting of organic solvents and oil.

5. The composition of claim 2 wherein said composition when placed into a sample of water containing contaminant reduces the amount of contaminant in said 2000 ml sample of water, wherein said contaminant is selected from the group consisting of polycyclic aromatic hydrocarbons, polychlorinated biphenyls, organic solvents and oil.

6. The composition of claim 1 wherein said composition comprises nutrients for said microbial agent.

7. The composition of claim 2 wherein said composition also comprises nutrients for said microbial agent.

8. The composition of claim 1 wherein said contaminant is petroleum hydrocarbons, and when said water comprises said contaminant as 23,880–24,360 mg/l of total petroleum hydrocarbons in water, with said contaminant-reducing agent present as $4 \times 10^6$ cfu/ml in fresh water for 21 days, total petroleum hydrocarbons in said water are reduced to 7740 mg/l or less.

9. The composition of claim 1 wherein said composition when placed into a sample of water containing contaminant reduces the amount of contaminant in said 2000 ml sample of water, wherein said contaminant is selected from the group consisting of polycyclic aromatic hydrocarbons, polychlorinated biphenyls, organic solvents and oil, said composition also comprises nutrients for said microbial agent, and when said contaminant is petroleum hydrocarbons, and when said water comprises said contaminant as 23,880–24,360 mg/l of total petroleum hydrocarbons in water, with said contaminant-reducing agent present as $4\times10^6$ cfu/ml in fresh water for 21 days, total petroleum hydrocarbons in said water are reduced to 7740 mg/l or less.

10. The composition of claim 9 wherein the contaminant-reducing composition is a composition which releases said microbial agent over time as said superabsorbent polymer swells in contact with water.

11. The composition of claim 1 wherein said polymer is capable of absorbing over five hundred times its weight in water.

12. The composition of claim 2 wherein said polymer is capable of absorbing over five hundred times its weight in water.

13. The composition of claim 3 wherein said polymer is capable of absorbing over five hundred times its weight in water.

14. The composition of claim 4 wherein said polymer is capable of absorbing over five hundred times its weight in water.

15. The composition of claim 1 wherein said polymer is capable of absorbing over one thousand times its weight in water.

16. The composition of claim 2 wherein said polymer is capable of absorbing over one thousand times its weight in water.

17. The composition of claim 3 wherein said polymer is capable of absorbing over one thousand times its weight in water.

18. The composition of claim 4 wherein said polymer is capable of absorbing over one thousand times its weight in water.

\* \* \* \* \*